(12) United States Patent
Colton et al.

(10) Patent No.: US 6,368,592 B1
(45) Date of Patent: Apr. 9, 2002

(54) METHOD OF DELIVERING OXYGEN TO CELLS BY ELECTROLYZING WATER

(75) Inventors: Clark K. Colton; Larry L. Swette, both of Newton, MA (US)

(73) Assignee: Massachusetts Institute of Technology, Cambridge, MA (US)

(*) Notice: Subject to any disclaimer, the term of this patent is extended or adjusted under 35 U.S.C. 154(b) by 0 days.

(21) Appl. No.: 09/356,079

(22) Filed: Jul. 16, 1999

Related U.S. Application Data

(60) Provisional application No. 60/093,147, filed on Jul. 17, 1998.

(51) Int. Cl.⁷ .......................... C12N 5/04; C12N 5/08; C12M 3/00; C12M 1/12; A61F 2/00
(52) U.S. Cl. ............... 424/93.7; 424/423; 435/325; 435/382; 435/383; 435/289.1; 435/297.1
(58) Field of Search ................... 435/325, 382, 435/383, 289.1, 297.1; 424/93.7, 423

(56) References Cited

U.S. PATENT DOCUMENTS

| | | | |
|---|---|---|---|
| 5,011,472 A | 4/1991 | Aebischer et al. | 604/50 |
| 5,085,656 A | 2/1992 | Polaschegg | 604/891.1 |
| 5,201,728 A | 4/1993 | Giampapa | 604/891.1 |
| 5,391,164 A | 2/1995 | Giampapa | 604/891.1 |
| 5,443,508 A | 8/1995 | Giampapa | 623/11 |
| 5,575,770 A | 11/1996 | Melsky, et al. | 604/93 |
| 5,788,682 A | 8/1998 | Maget | 604/290 |
| 5,814,020 A | 9/1998 | Gross | 604/41 |
| 5,848,991 A | 12/1998 | Gross et al. | 604/140 |
| 5,855,570 A | 1/1999 | Scherson et al. | 604/304 |
| 5,891,097 A | 4/1999 | Saito et al. | 604/141 |
| 5,899,381 A | 5/1999 | Gordon et al. | 239/6 |
| 5,914,199 A | 6/1999 | Carter et al. | 429/25 |
| 5,916,505 A | 6/1999 | Cisar et al. | 264/85 |
| 5,921,251 A | 7/1999 | Joshi | 132/112 |
| 5,928,194 A | 7/1999 | Maget | 604/141 |
| 5,938,640 A | 8/1999 | Maget et al. | 604/145 |
| 5,945,766 A | 8/1999 | Kim et al. | 310/268 |
| 5,951,538 A | 9/1999 | Joshi et al. | 604/500 |
| 5,957,895 A | 9/1999 | Sage et al. | 604/181 |
| 5,961,796 A | 10/1999 | Hitchens et al. | 204/252 |
| 5,971,722 A | 10/1999 | Maget et al. | 417/379 |

OTHER PUBLICATIONS

Humes, (ed.) "Application of Gene and Cell Therapies in the Tissue Engineering of a Bioartifical Kidney." The International Journal of Artificial Organs 19 (4):215–217 (1996).

Colton, "Engineering Challenges in Cell–Encapsulation Technology." Trends In Biotechnology 14: 158–162 (1996).
Colton, "Implantable Biohybrid Artifical Organs." Cell Transplantation 4 (4): 415–436 (1995).
Colton, "Quantitation of Membrane Biocompatibility." Contributions to Nephrology 59: 110–125 (1987).
Davis, et al., "Toward Development of an Implantable Tissue Engineered Liver." Biomaterials 17 (3): 365–372 (1996).
Drake et al., "A Tissue Implantable Fuel Cell Power Supply." Transactions American Society for Artificial Internal Organs 16: 199–206 (1970).
Wang, "New Technologies for Bioartificial Organs." Artificial Organs 22 (1): 68–74 (1998).
Yomtov, et al., "Implantable Monitoring Systems." Journal of Electrocardiology 27 (Suppl): 74–77 (1997).
Suzuki, et al., "Function and Survival of Macroencapsulated Syngeneic Islets Transplanted Into Streptozocin–Diabetic Mice." Transplantation 66 (1): 21–28 (Jul. 15, 1998).
Suzuki, et al., "Number and Volume of Islets Transplanted in Immunobarrier Devices." Cell Transplantation 7 (1): 47–52 (1998).
Righetti, et al., "An Isoelectrically Trapped Enzyme Reactor Operating in An Electric Field." Electrophoresis 19 (7): 1075–1080 (Jun. 1998).
Avgoustiniatos, et al., "Effect of External Oxygen Mass Transfer Resistances on Viability of Immunoisolated Tissue." Bioartificial Organs 831: 145–167 (1997).

*Primary Examiner*—David M. Naff
(74) *Attorney, Agent, or Firm*—Testa, Hurwitz & Thibeault, LLP

(57) ABSTRACT

Oxygen is supplied to cells in vitro or in vivo by generating oxygen with an oxygen generator that electrolyzes water to oxygen and hydrogen. Oxygen can be generated substantially without generating free hydrogen using a multilayer electrolyzer sheet having a proton exchange membrane sandwiched by an anode layer and a cathode layer. The oxygen generator may be used to supply oxygen to cells contained by a culture plate, a culture flask, a microtiter plate or an extracorporeal circuit, or to cells in an encapsulating chamber for implanting in the body such as an immunoisolation chamber bounded by a semipermeable barrier layer that allows selected components to enter and leave the chamber. A bioactive molecule may be present with the cells. Oxygen can be delivered in situ to cells within the body such as by implanting the oxygen generator in proximity to cell-containing microcapsules in an intraperitoneal space, or by implanting a system containing the oxygen generator in proximity to an immunoisolation chamber containing cells.

15 Claims, 11 Drawing Sheets

METHOD OF DELIVERING OXYGEN TO CELLS BY ELECTROLYZING WATER

CROSS-REFERENCE TO RELATED APPLICATION

This application claims priority under 35 U.S.C. 35 §119 (e) to U.S. Provisional Application 60/093,147, filed Jul. 17, 1998, the entire disclosure of which is incorporated herein by reference.

GOVERNMENT SUPPORT

This invention was made with government support under Grant Numbers NIH- 1R01-HD31443 and 1 R43 DK51909-01 awarded by the National Institutes of Health. The government has certain rights in this invention.

FIELD OF THE INVENTION

The invention relates generally to devices for delivering oxygen to cells and more specifically to devices which deliver oxygen in situ to cells in the body of an organism.

BACKGROUND

Techniques to transplant cells into people in need of the functions that these cells provide have application in the treatment of a variety of chronic conditions including diabetes, hemophilia, dwarfism, anemia, kidney failure, hepatic failure, familial hypercholesterolemia, immunodeficiency disorders, pituitary disorders, and central nervous system disorders.

Cell implantation techniques are typically limited by shortages of cells. For example, successful transplantation of insulin-secreting cells or tissue into people with diabetes has been a challenge because of the obvious shortage of human islet tissue. The approximately 3000 cadaver pancreases that could be available each year in the U.S.A. come nowhere near to meeting the needs of people with Insulin Dependent Diabetes Mellitus (IDDM). Use of cells/tissue from other species as xenogeneic cells may therefore provide the fastest path to clinical application.

Immunobarrier devices have been developed as a means of protecting xenogeneic cells from transplantation rejection by a host organism. The xenogeneic cells are encapsulated at a high, tissue-like density or are dispersed in the form of individual cells or cell aggregates (e.g., islets of Langerhans) in an extracellular gel matrix such as agar, alginate, or chitosan, within these devices.

High-density culture, if attainable, is advantageous because it minimizes the size of the implanted device used in a particular application. This is desirable because the complexity and difficulty of the application increases with the volume of implanted cells/tissue. Consequently, applications which have tended to require the least amount of transplanted cells/tissue, such as central nervous system applications, have been the first to advance to clinical testing.

Maintenance of the viability and function of implanted cells within an immunobarrier device is essential and limited by the supply of nutrients and oxygen which can be provided to the cells from the host. Apoptosis in transplanted tissues has been observed and may be a general response to severe hypoxia, as well as to methods of isolation and culture, glycemic state, and the nonspecific inflammatory reaction associated with the transplantation procedure.

The impact of hypoxia is also influenced by the type of cells/tissues being implanted. For example, pancreatic islet cells are especially prone to oxygen supply limitations because they have a relatively high oxygen consumption rate. They are normally highly vascularized and are supplied blood at arterial $pO_2$. When cultured in vitro under normoxic conditions, islets develop a necrotic core, the size of which increases with increasing islet size, as is to be expected as a result of oxygen diffusion and consumption within the islet. However, the death of implanted cells due to hypoxia is not the only concern. Oxygen levels high enough to keep cells alive can nonetheless have deleterious effects on cell functions that require higher cellular ATP concentrations, for example, ATP-dependent insulin secretion.

Only scant attention has been paid to the issue of islet viability within implanted immunobarrier devices. However, recently, critical parameters such as the number and volume of viable islet cells that can be supported by such devices, and the development of islet necrosis and fibrosis in such devices has begun to be examined. It is clear from these recent studies that all attempts to support larger volumes of islet tissue in high-density culture (i.e., where all or most of the internal device volume is occupied by viable islet tissue) have led to massive islet necrosis, invariably in regions furthest from the oxygen source. As with transplantation of naked cells, the hypoxic environment for several days following transplantation appears to be a critical problem. For example, most of the loss of viable β-cell mass undoubtedly occurs during the first few days after transplantation within these devices.

With few exceptions, only by suspending islets in an extracellular gel matrix at very low islet volume fractions (e.g., 1 to 5%), which greatly increases the size of the implanted device, have investigators been able to maintain the viability of the initially loaded islets. However, use of such low tissue density puts undesirable constraints on the maximum number of islets that can be supported in a device of a size suitable for surgical implantation.

Attempts to modify the design of immunobarrier devices have been made to try to overcome these limitations. A biohybrid artificial pancreas for insulin secretion known in the art consists of a semipermeable membrane tube through which arterial blood flows. The membrane tube is surrounded by the implanted tissue which is, in turn, contained in a housing. This approach provides the highest available $pO_2$ (100 mm Hg) but suffers from the need to open the cardiovascular system; thus, it may be limited to only a small fraction of patients.

One alternative is an extravascular device in the form of a planar or cylindrical diffusion chamber implanted, for example, in subcutaneous tissue or intraperitoneally. Such devices are exposed to the mean $pO_2$ of the microvasculature (about 40 mm Hg) limiting the steady state thickness of viable tissue that can be supported. Further limits are imposed when such devices are implanted into soft tissue. If a foreign body response occurs, an avascular fibrotic tissue layer adjacent to the chamber can be produced, typically on the order of 100 μm thick. This fibrotic tissue increases the distance between blood vessels and implant, and the fibroblasts in fibrotic tissue layer also consume oxygen. Oxygen deficits are especially likely during the first few days after implantation before neovascularization has a chance to occur. Anoxia may exist within regions of the device, leading to death of a substantial fraction of the initially implanted tissue.

Microporous membranes that induce neovascularization at the device-host tissue interface have also been used. This angiogenic process takes 2–3 weeks for completion, and the vascular structures induced remain indefinitely. By bringing some blood vessels close to the implant, oxygen delivery is improved. Oxygen delivery also may be improved by pre-vascularizing the device, e.g, by infusion of an angiogenic factor(s) through the membranes into the surrounding tissue.

Another means of implanting cells in an extravascular environment involves the use of spherical microcapsules. The microcapsules comprise small quantities of cells enclosed in a semipermeable membrane and can be implanted in an extravascular space, for example, in the peritoneal space. However, the large volume of microcapsules employed, and the tendency for most to permanently attach to peritoneal surfaces, may lead to clinical problems. Thus, despite encouraging results with various tissues and applications, the problem of oxygen transport limitations remain.

The present invention improves the viability and function of encapsulated tissue.

SUMMARY OF THE INVENTION

The invention provides an oxygen generator device for delivering oxygen to cells or to a cell compatible fluid. The oxygen generator device disclosed herein has application for in vitro or in vivo use. In one aspect the device is placed in proximity to a cell compatible fluid. In another aspect, the oxygen generator is placed in proximity to cells for which supplemental oxygen is desired. In a further aspect of the invention, the oxygen generator is placed in proximity to a cell encapsulating device. The oxygen generator disclosed herein provides a system to deliver oxygen to cells in situ in the body of an organism.

In one embodiment of the invention, the oxygen generator is an electrolyzer device which electrolyzes water into oxygen and hydrogen. In another embodiment of the invention, the oxygen generator is in the form of a thin, multilayer electrolyzer sheet and is permeable to gas and water vapor but impermeable to liquids and dissolved material. In a further embodiment of the invention, the oxygen generator comprises a multilayer electrolyzer sheet having a proton exchange membrane sandwiched by an anode layer and a cathode layer. In a further embodiment of the invention, the device comprises a multilayer electolyzer sheet adapted for mating to a container containing cells.

In one embodiment of the invention, the oxygen generator is in communication with an energy source, such as a battery. In another embodiment of the invention, the battery is rechargeable transcutaneously. In a further embodiment of the invention, the battery is recharged using a transcutaneous energy transfer system (TET) system. In a further embodiment, the invention may be operated directly and continuously from a battery-powered TET system.

In one embodiment of the invention, the oxygen generator is provided in proximity to cells in vitro. The oxygen generator is provided, either within a container containing the cells, or as an integral part of the container. In one embodiment of the invention, the oxygen generator is provided, either within, or as an integral part of, a cell-containing cartridge in an extracorporeal circuit device.

In a further embodiment of the invention, the oxygen generator is provided as an in-line oxygenator through which blood, plasma, and other bodily fluids may flow. In this embodiment, the oxygen generator is mated to, contained within, or is an integral part of, a hollow tube through which blood, plasma, and other bodily fluids, or culture medium may flow.

In one embodiment, the invention provides a system for delivering oxygen in situ to cells within the body of an organism. In this embodiment of the invention, the system comprises an oxygen generator positioned in proximity to a cell encapsulating chamber and is implanted within the body of an organism. The cell encapsulating chamber comprises a containment space for cells bounded by a semipermeable barrier layer which acts as a selective diffusion layer, allowing selected components to enter and leave the cell encapsulating chamber.

In a further embodiment of the invention, the system includes an oxygen generator which comprises a multilayer electrolyzer sheet mated to a cell encapsulating chamber comprising two semipermeable membranes sealed together by a ring seal.

In another embodiment of the invention, the system for delivering oxygen in situ comprises a cell encapsulating chamber which defines an immunoisolation chamber. In this embodiment, the semipermeable barrier layer of the immunoisolation chamber immunoisolates cells contained within the chamber when the device is exposed to components of the immune system. In a further embodiment, the invention relates to a system implantable in the body of an organism for growing tissue in immunoisolation while providing supplemental oxygen to the tissue.

In another embodiment of the invention, the system for delivering oxygen in situ comprises an oxygen generator provided in proximity to, or mated with, a semipermeable membrane tube through which blood, plasma, and other bodily fluids may flow. In another embodiment of the invention, the membrane tube is surrounded by implanted tissue. In a further embodiment of the invention, the membrane tube and tissue is contained within a housing.

The invention also relates to a system for delivering oxygen in situ to cells which are not contained within a cell encapsulating device. In a one embodiment of the invention, the system for delivering oxygen in situ comprises an oxygen generator placed in proximity to cell-containing microcapsules which are free to migrate within an intraperitoneal space. In another embodiment of the invention, the system comprises an oxygen generator positioned in proximity to a cell-supporting, biocompatible, polymeric scaffold within the body of an organism. In this embodiment, the oxygen generator can be used to maintain, and support the growth of artificial tissues.

In a further embodiment of the invention, two oxygen generators are placed back to back with cells on both sides of the oxygen generator, maximizing the amount of oxygen that can be delivered to cells.

In another embodiment, the system is designed to deliver oxygen in situ to cells located at a distance from the oxygen generator. A tube with low oxygen permeability is attached to the oxygen generator. Generated oxygen is transferred through the tube to a flexible oxygen distributor fabricated from oxygen-permeable membranes. In one aspect of the invention, the oxygen distributor is placed in proximity to cells, tissues, or organs, for which supplemental oxygen is desired. In another aspect of the invention, the oxygen distributor is placed in proximity to a cell encapsulating device. The flexible oxygen distributor provides a means to deliver oxygen from an oxygen generator located at a distance to cells, tissues, or organs located anywhere, and having any shape, within the body of an organism.

In a further embodiment of the invention, the oxygen generator is an oxygen transfer device which electrochemically transfers oxygen from the cathode side to the anode side of the oxygen generator substantially without the generation of hydrogen.

The invention also relates to methods of delivering oxygen to cells in vitro comprising positioning an oxygen generator in proximity to the cells. In one embodiment of the invention, the method comprises delivering oxygen to cells contained within a container, such as a cell culture dish or a flask. In another embodiment of the invention, the method comprises placing an oxygen generator in proximity to the cells within a cell-containing cartridge in an extracorporeal circuit or in culture medium in a perfusion circuit. In another embodiment of the device, the oxygen generator is provided as an in-line oxygenator through which culture medium flows. In this embodiment, oxygenated culture medium flows through the cell-containing cartridge and is then discarded or recycled through the oxygenator for reoxygenation. In a further embodiment of the invention, the oxygenated culture medium is made to flow in and around an organ for transplantation, such as heart, kidney, liver, or pancreas, during the period when it is stored or shipped.

The invention also relates to a method of delivering oxygen in situ to cells within a body of an organism. In this embodiment of the invention, an oxygen generator is placed in proximity to cells which are free to migrate within an intraperitoneal space. In another embodiment of the invention, the method includes implanting a system within the body of an organism, the system comprising an oxygen generator which is in proximity to a cell encapsulating chamber, such as an immunoisolation chamber.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

FIG. 10a shows cells after four days in the absence of in situ oxygen generation (with the oxygen generator disconnected from its power source). FIG. 10b shows cells after four days with in situ oxygen generation (with the oxygen generator connected to its power source).

DETAILED DESCRIPTION

Figure 1:
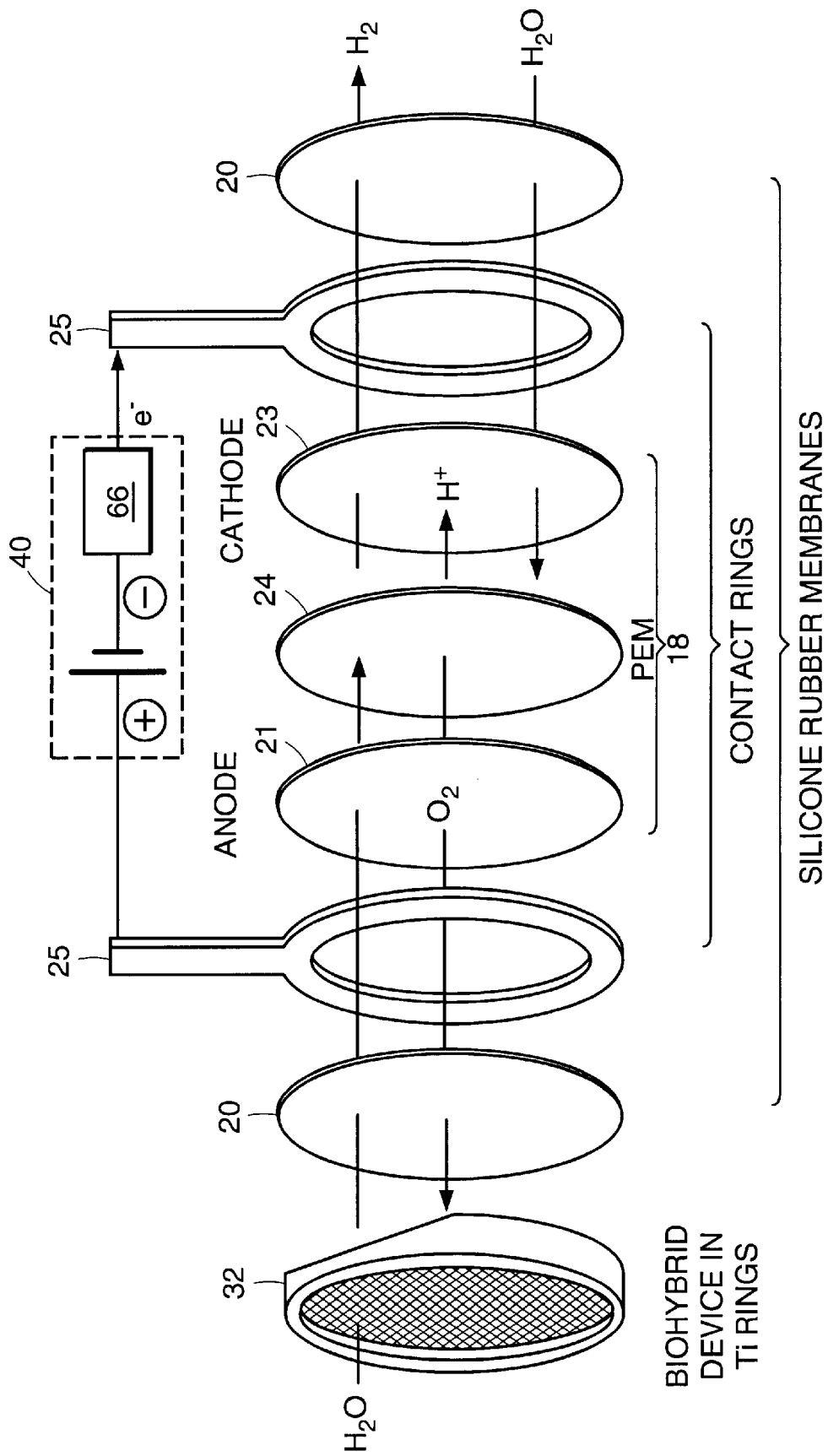
FIG. 1 is a schematic diagram of an oxygen generator according to one embodiment of the invention.

The invention relates to an oxygen generator which may be used to deliver oxygen to cells in vitro or in vivo. FIG. 1 is an exploded schematic diagram of the components of an oxygen generator (electrolyzer) 18, according to one embodiment of the invention, that carries out electrolysis of water. The water is obtained from a cell compatible media, i.e., cell culture media (synthetic or natural), or bodily fluids, such as blood or plasma.

The oxygen generator 18 comprises two catalytic electrodes, i.e., an anode 21 and a cathode 23, separated by a solid polymer electrolyte proton exchange membrane (PEM) 24 which allows passage of hydrated H$^+$ but has much lower permeability to gases such as O$_2$ and H$_2$. As a consequence, the half-cell reactions at each electrode (21 and 23) are compartmentalized. For normal acid electrolysis, the reactions are

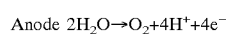
Anode $2H_2O \rightarrow O_2 + 4H^+ + 4e^-$

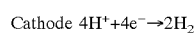
Cathode $4H^+ + 4e^- \rightarrow 2H_2$

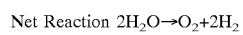
Net Reaction $2H_2O \rightarrow O_2 + 2H_2$

O$_2$ is formed at the anode 21. H$^+$, which is also formed at the anode 21, is transported through the PEM 24 under the influence of a potential gradient imposed by a constant current controller 66 in an external circuit 40 shown in phantom in FIG. 1. The hydrogen ions arriving at the cathode 23 recombine with electrons passed through the external circuit 40 from the anode 21 so as to form molecular hydrogen.

Because of the permeability properties of the PEM 24, virtually all of the O$_2$ diffuses into the cells in proximity to the oxygen generator 18, whereas the H$_2$ diffuses away from the oxygen generator 18. The quantity of hydrogen generated is expected to be less than the stoichiometric 2:1 ratio relative to oxygen for normal electrolysis because oxygen diffusing into the cathode 23 side of the oxygen generator 18 from the cell media is preferentially reduced as compared to H$^+$. With oxygen present at the cathode 23, the reaction

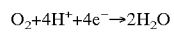
$O_2 + 4H^+ + 4e^- \rightarrow 2H_2O$ competes with the reaction

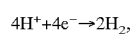
$4H^+ + 4e^- \rightarrow 2H_2$, thereby decreasing the net hydrogen production. The extent of the decrease in net hydrogen production increases with an increase in the rate at which oxygen reaches the cathode surface.

In another embodiment of the invention, both electrodes, 21 and 23, are covered by silicone rubber membranes 20, so that water enters the oxygen generator 18 only in its vapor form and the interior of the oxygen generator 18 is kept free of all other components of biological fluids. In a further embodiment of the invention, metal contact rings 25 are provided which provide connections to the external circuit 40.

Figure 2:
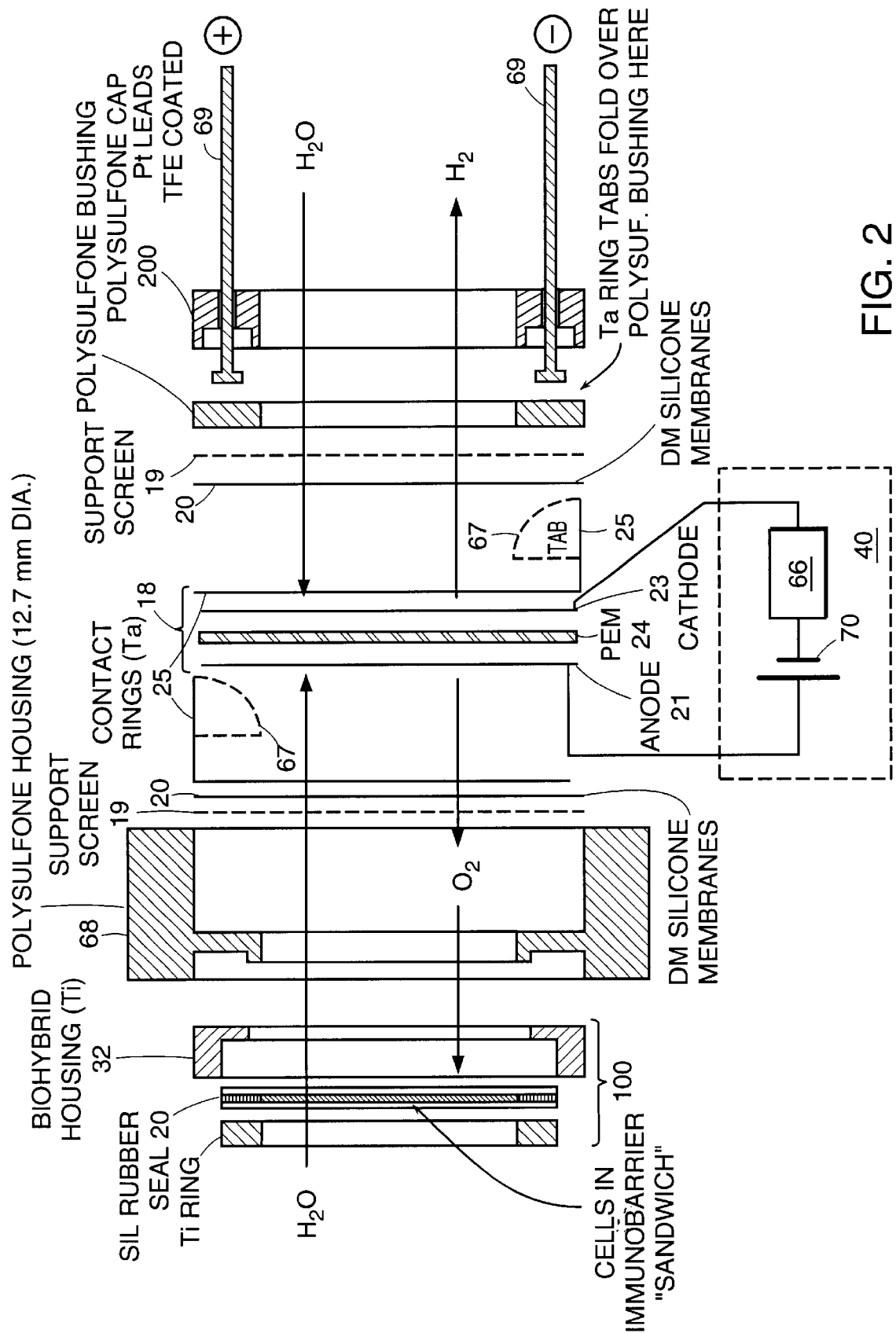
FIG. 2 is a schematic diagram of a system comprising an oxygen generator in proximity to a cell encapsulating chamber in an in vitro embodiment of the invention.

An oxygen generator 18 according to another embodiment of the invention is shown in FIG. 2. The active components of the oxygen generator 18 are the catalytic electrodes, 21 and 23, and the PEM 24. In one embodiment of the invention, the PEM 24 is Nafion 117 (1100 equivalent weight, about 1250 μm thick hydrated, DuPont Co., Wilmington, Del.) which has $O_2$ and $H_2$ permeabilities more than two orders of magnitude less than silicone rubber. The Nafion membrane is received in the $Na^+$ form and is exchanged in acid to convert it to the proton form. The electrodes 21 and 23 are placed in intimate contact with the PEM 24.

In a further embodiment of the invention, a substrate is provided for the electrodes, anode 21 and cathode 23, in the form of a very fine platinum (Pt) screen (150 mesh with 43-μm diameter wire). The cathode 23 catalyst is Pt(25 $m^2/g$), and the anode 21 catalyst is Pt-iridium oxide (100 $m^2/g$). The platinum screens comprise high surface area particles mixed with polytetrafluoroethylene (PTFE) particles and pressed onto a fine-mesh substrate screen which in turn is pressed onto the PEM 24.

To make electrical contact with the electrodes 21 and 23, contact rings 25 are provided which comprise rings of tantalum foil, provided with a tab 67, resistance welded to the edge of the electrodes 21 and 23 before bonding to the PEM 24. The silicone rubber membranes 20 are then hot pressed on either side of the contact rings 25. In a further embodiment of the invention, a disk of fine mesh support screen 19 comprising a biocompatible, inert metal (e.g., titanium) is added over the outside of the silicon rubber membranes 20. In one embodiment of the invention, the entire thickness of the oxygen generator, including the silicon rubber membranes 20 and outer support screens 19, is about 0.75 mm.

In another embodiment of the invention, oxygen generator 18 is enclosed in a housing 68 (e.g., a polysulfone housing) incorporating wire leads 69 for connection to a current control circuit 40 and a power supply 70 (the current control circuit and power supply are shown in phantom in FIG. 2). In a further embodiment of the invention, the housing 68 is adapted for coupling to a container 100, which may be mated to the housing 68 at one face of the housing 68.

In operation, the oxygen generator 18 is provided in communication with a power supply 70 and a constant current controller 40, in order to maintain a constant rate of oxygen generation in the presence of resistance variations in the oxygen generator 18 and declining battery voltage (when a battery/energy source 199 is used). In one embodiment of the invention, a constant current control 40 is implemented with a Howland circuit, a voltage-controlled current source which utilizes positive and negative feedback to provide precise current control. In a further embodiment of the invention, the current control circuit 40 is powered by an AC-DC converter or by a single battery/energy source 199. In a further embodiment of the invention, a potentiometer is provided to adjust current from about 0 to about 200 μA.

In a further embodiment of the invention, the oxygen generator 18 is an oxygen transfer device, in which hydrogen generation at the cathode 23 is suppressed, when the cathode 23 has access to a continuous supply of oxygen, such as air or dissolved oxygen, at a rate in excess of the oxygen generation rate at the anode 21. Oxygen is preferentially reduced at the cathode 23, when available, in lieu of the reduction of protons to hydrogen in the pure electrolysis reaction; the same oxygen generation reaction occurs at the anode in both cases.

In a further embodiment of the invention, the oxygen generator 18 is an oxygen transfer device in which hydrogen generation at the cathode 23 is suppressed by an alternative means; the oxygen generator 18 is made to have a larger geometric area than the cell encapsulating chamber 10, thereby providing the cathode 23 with access to dissolved oxygen in excess of the oxygen generation rate at the anode 21.

The oxygen generation rate M (mol/s) of the oxygen generator 18 is related to the applied current I (A) by $$I = n\, F\, M \quad (1)$$

where n=4 is the number of electrons required to make one molecule of oxygen, and F is Faraday's constant (96,500 A·s/equivalent). The imposed flux of oxygen $N_e$ from the oxygen generator/electrolyzer 18 into the cell encapsulating chamber/planar diffusion chamber 10 (mol/$cm^2$·s) is $$N_e = \frac{M}{A_e} \quad (2)$$

where $A_e$=0.317 $cm^2$ is the cross-sectional area of the gap between the oxygen generator/electrolyzer 18 and the cell encapsulating chamber/diffusion chamber 10. Equation (2) can thus be written as $$i = n\, F\, N_e \quad (3)$$

where $i = I/A_e$ is the effective current density at the electrodes 21 and 23.

The oxygen generator 18 disclosed herein may be used in a variety of in vitro and in vivo applications. In one embodiment of the invention, the oxygen generator 18 is provided in proximity to cells in vitro, and is either contained within, or is an integral part of the container 100. Types of containers 100 encompassed within the scope of the invention include, but are not limited to, cell culture plates, flat-bottom tissue culture flasks, roller cell culture flasks, microtiter plates, and the like. In this embodiment of the invention, the oxygen generator 18 may be used to provide supplemental oxygen to cells in culture and may be used to enhance the proliferation of these cells. In another embodiment of the invention, the container 100 further comprise an oxygen sensor or other type of biosensor to monitor the level of metabolites in the cell media in which cells are cultured.

In another embodiment of the invention, the oxygen generator 18 is positioned in proximity to cells within the cell-cartridge of an extracorporeal circuit device or within a cell cartridge in a cell perfusion circuit. Such devices are well known in the art. In a further embodiment of the invention the oxygen generator provides oxygen which delivers oxygenated fluids to cells and does not have to be in proximity to the cells themselves. In this embodiment of the invention, the oxygen generator is either mated to, contained within, or is an integral part of, a hollow tube, flat plat channel or other conduit through which cell compatible media, such as cell culture media, plasma, blood, and the like, may flow.

The invention also relates to a system for delivering oxygen in situ to cells within the body of an organism. In this embodiment of the invention, the system (shown in FIG. 3) comprises an oxygen generator 18 positioned in proximity to a cell encapsulating chamber 10 and is implanted within the body of an organism. The cell encapsulating chamber 10 comprises a containment space for cells bounded by a semipermeable barrier layer 9 which acts as a selective diffusion layer, allowing selected components to enter and leave the cell encapsulating chamber 10. The oxygen generator 18 enhances the viability and/or proliferation of cells 14 within the containment space. In a second embodiment of the invention, the oxygen generator 18 includes an energy source 199 (e.g., a battery, current controller, fuel cell, and the like).

The system may be used to deliver cells 14 which can provide a function lacking in a body of a patient. The function may be naturally provided by these cells 14, or the cells 14 may be genetically modified to provide the function. The system may be used in methods of treatment of conditions, especially chronic conditions, including, but not limited to, the treatment of diabetes, hemophilia, dwarfism, anemia, kidney failure, hepatic failure, immunodeficiency disorders, pituitary disorders, and central nervous system disorders. Nervous system disorders which may be treated include, but are not limited to, chronic pain, Parkinson's disease, Alzheimer's disease and amyotrophic lateral sclerosis. The cells 14 may come from a variety of sources, including, but not limited to, pancreas cells, hepatocytes, kidney cells, lung cells, neural cells, pituitary cells, parathyroid cells, thyroid cells, and adrenal cells. Multiple types of cells 14 may be mixed in a single cell encapsulating chamber 10 (e.g., hepatocytes and pancreas cells may be provided within a single isolation chamber 10). As used herein, the term "cells" 14 encompasses individual or isolated cells, cell lines, tissues, such as islets, and cell aggregates. In an embodiment of the invention, a bioartificial organ is provided. As used herein, the term "bioartificial organ" encompasses any device that incorporates both synthetic and living material.

In one embodiment of the invention, the βTC3 cell line is used as a source of cells 14. βTC3 cells are derived from an insulinoma from a transgenic β6DZF1 mouse carrying a hybrid insulin-promoted SV40 T-antigen gene. The βTC3 line is among those genetically engineered β-cell lines which can be used for the treatment of diabetes.

The concentration of cells 14 required for transplantation is determined by the secretion rate of the desired agent by the cell 14 and the amount of active agent required by the body. For example, the average patient with IDDM requires approximately 30 Units of insulin per day to control blood glucose levels. The amount of insulin (Units/cells/day) produced by a population of islet cells is then determined in culture and the number of transplanted 14 needed to provide the patient's required insulin dose is loaded within the immunoisolation chamber 10. Typically, this is on the order of about $10^9$ cells 14. In the case of cells 14 that proliferate, a determination of the insulin production rate in culture permits an estimation of the number of cells 14 required in a given volume within a cell encapsulating chamber 10. A small number of cells 14 can be used which will then proliferate to fill the volume of the chamber 10 and provide the necessary amount of insulin. It is readily apparent, that similar calculations may be performed for any application for which a required dosage of active agent is known, or is determinable, and for which the amount of bioactive agent produced by cells 14 may be measured.

In addition to cells 14, the system may be used to deliver a variety of bioactive molecules, including derivatives, analogs, and active fragment of these molecules. Bioactive molecules include, but are not limited to, hormones, growth factors, cytokines, vascularizing agents, receptors, ligands, antibodies, antibody fragments, fusion proteins, peptides (natural or synthetic), drugs, nucleic acids (including naked DNA, DNA encapsulated in liposomes, viral particles, or microspheres, antisense molecules, ribozymes, triple helix DNA, PNA molecules, and aptamers). Autologous molecules, as would be generated by tissues derived from transgenic animals, can be used to minimize immune responses by the host organism. While the system provides a means to immunoisolate transplanted living cells 14 and to prevent the immune system of the recipient organism from attacking the transplanted cells 14, the system may also be used as a bioreactor in in vitro applications.

In a further embodiment of the invention, the disclosed system provides a cell encapsulating chamber 10 which immunoisolates transplanted cells 14 by surrounding cells 14 with a semipermeable barrier layer 9. The semipermeable barrier layer 9 protects the transplanted cells 14 from components of both the cellular and humoral immune system but permits passage of the agent of interest, for example, secreted insulin. The transport properties of the implanted cells 14, semipermeable barrier layer 9, and surrounding host cells/tissue/fluids must permit a sufficient supply of nutrients and oxygen, as well as the removal of metabolic waste products, by diffusion from, or to, the nearest blood supply.

As used herein, the term "semipermeable barrier layer" 9 includes biocompatible encapsulants, such as membranes, which provide a selective diffusion layer which controls the entry and exit of molecules into and out of the cell encapsulating chamber 10. Minimally the barrier layer 9, must be have a pore size, pore density, percent porosity, molecular weight cut off to keep cells within the cell encapsulating chamber 10. Particularly in embodiments where allogeneic or autologous cells 14 are transplanted, the pore size may be quite large as about 0.1 μm but must completely prevent passage of cells 14. In the embodiment of the invention where the cell encapsulating chamber 10 is a xenogeneic immuonisolation chamber, the membranes may have any type of pore size, pore density, percent porosity, molecular weight cutoff, sufficient to keep selected components of the immune system out, yet allowing for the transport of nutrients, oxygen, secreted cellular products (e.g., secreted insulin), metabolic wastes, ions, and other bioactive molecules. When xenogeneic cells 14 are used, the molecular weight cutoff should be about 100,000 daltons or less, so as to prevent components of the humoral immune system from entering into the cell encapsulating chamber 10 and to prevent endogenous retroviruses transmittable by the cells 14, or other infectious macromolecules which might be secreted by the cells, from exiting the cell encapsulating chamber 10.

Semipermeable barrier layer 9 material is selected from the group including, but not limited to, acrylic, polyurethanes, cellulose acetate, agar, alginate, chitosan, or other types of hydrogels, polysulfone, polyether sulfones, polyvinyl chloride, polyvinyl alcohols, polyvinylidene fluoride, polytetrafluoroethylene, polyacryl nitrites, and including derivatives, and/or mixtures thereof. Any porous polymeric material is encompassed within the scope of the invention which has the desired membrane strength (i.e., ability to survive handling, transplantation, and the environment inside the body) and the desired permeability. The cell encapsulating chamber 10 is preferably easily removable from the body and replaceable in the body.

Figure 6:
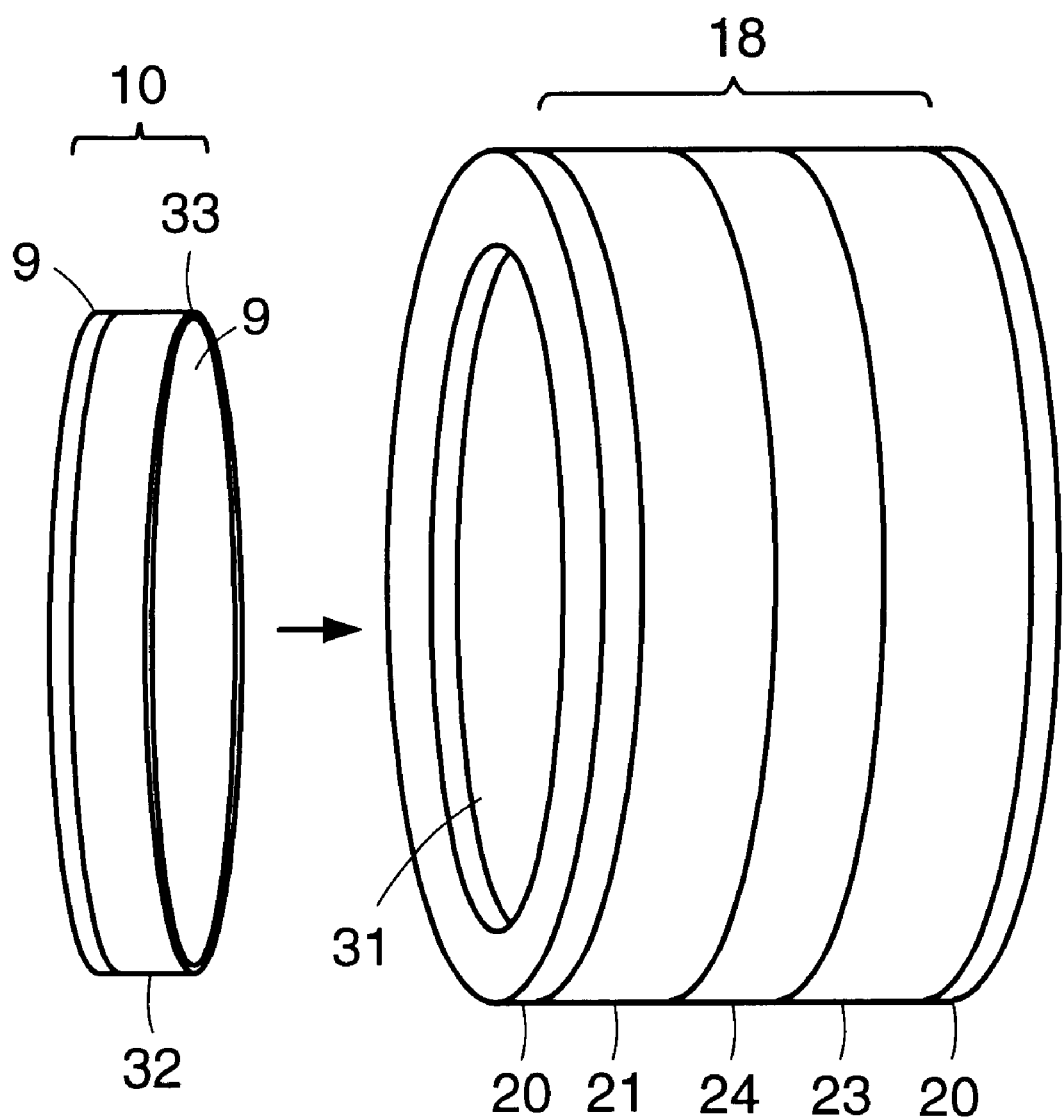
FIG. 6 is a schematic diagram of a ring cell encapsulation chamber according to one embodiment of the invention.

The cell encapsulating chamber 10 can be a variety of shapes including tubes or cylinders, cubes, spheres, discs, or sheets, so long as it is able to provide a sufficient containment surface for the number of cells 14 suitable for a given application. In one embodiment (shown in FIG. 6), the cell encapsulating chamber 10 is a ring chamber which includes two thin disc-shaped semipermeable barrier layer 9 membranes sealed together on their circular periphery by a ring seal 32. Suitable ring seal 32 materials include, but are not limited to, biocompatible, noncorrosive metals (e.g., titanium), Teflon®, plastic and the like. In this configuration, the space between the two semipermeable barrier layer 9 membranes contains the cells 14 to be implanted. The semipermeable barrier layer 9 membranes are both distensible and conformable. Distensible semipermeable barrier layer 9 membranes allow for the expansion of the cell encapsulating chamber 10, which is important when proliferating cell lines are used. When islets are the source of cells 14, the conformable semipermeable barrier layer 9 membranes partially conform to the shape of the cells 14, leading to a structure akin to peanut brittle. In a further embodiment of the invention the oxygen generator 18 can be provided proximal to, mated with, or an integral part of, a hollow tube through which blood flows. In this embodiment of the invention, cells 14 are implanted outside the tube. In a further embdiment of the invention, the cells 14 are surrounded by a housing.

Figure 3:
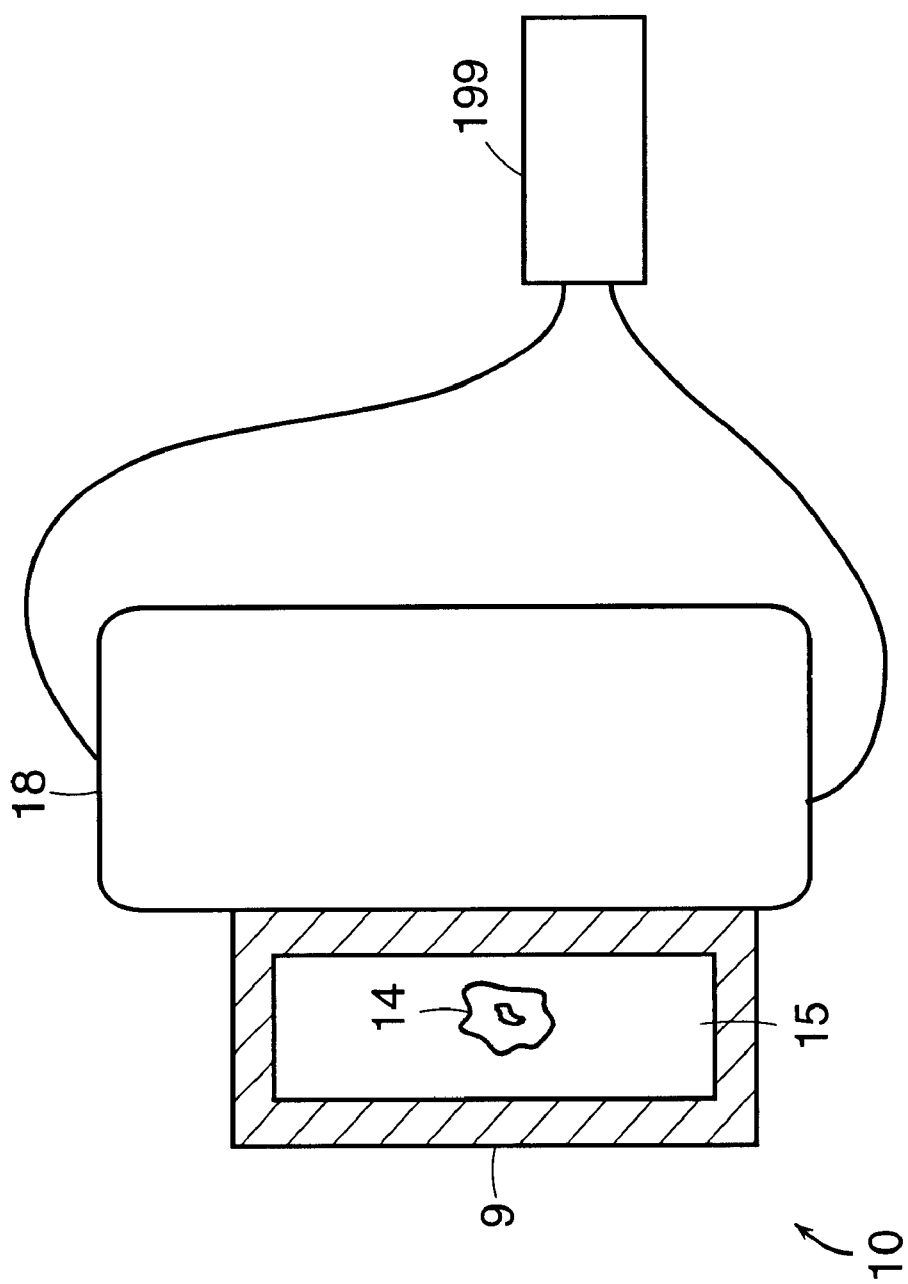
FIG. 3 is is a schematic diagram of a system comprising an oxygen generator in proximity to a cell encapsulating chamber in an in vivo embodiment of the invention.

The semipermeable barrier layer 9 of the cell encapsulating chamber 10 may be coated by other biocompatible molecules on the interior (i.e., the side proximal to the encapsulated cells 14), such as polymeric scaffolds which may also be coated by bioactive molecules such as ECM proteins, morphogenic proteins, growth factors, cytokines, and/or polysaccharides. As shown in FIG. 3, the interior of the semipermeable barrier layer 9 membrane in one embodiment further includes a gel matrix 15 (e.g., agar, alginate, chitosan, polyglycolic acid, polylactic acid, and the like) in which the cells 14 are embedded. In another embodiment, cells 14 in the cell encapsulating chamber 10 may themselves be encapsulated within microcapsules. The semipermeable barrier layer 9 membrane may also be coated with an anti-microbial and/or an anti-thrombotic agent on its outside surface.

The present invention provides a means of minimizing the size of a cell encapsulating device 10. For illustrative purposes, consider a planar diffusion immunoisolation chamber and the limiting case in which islet cells 14 occupy all available internal volume. The surface area A required by the device is given by A=V/h, where V is the required islet volume and h is the maximum total thickness of tissue that can be supported. If V=1 $cm^3$ and h=50 $\mu m$, then A=200 $cm^2$ (about 5.6 inches square). If enhanced oxygen delivery allows an increase to h=200 $\mu m$, then A=50 $cm^2$ (about 2.8 inches square). This reduction in required area makes it feasible to implant a single or small number of planar immunobarrier device(s).

The present invention thus provides a solution to two practical problems: reduction of the size of the cell encapsulating chamber 10 so that it can be implanted in a human, and minimization of the cost of the implantable tissue (e.g., islet tissue) by maximizing the number of cells 14 that can survive implantation.

The present invention supplements oxygen provided to isolated cells 14 by the blood stream by providing an oxygen generator 18 in close proximity to the cell encapsulating chamber 10. As used herein, the term "close proximity" refers to a distance through which sufficient oxygen can diffluse to enhance cell 14 viability and/or proliferation within the cell encapsulating chamber 10 in comparison with a device lacking an oxygen generator 18. In one embodiment of the invention, the oxygen generator 18 is adjacent to the cell encapsulating chamber 10.

In one embodiment of the invention, the system for providing an oxygen to cells in situ comprises an oxygen generator 18 which is a multilayer electrolyzer, of the type discussed above, comprising an anode layer 21 and a cathode layer 23 sandwiching a proton exchange membrane 24. Oxygen is supplied to implanted tissue by diffusion from the host side and the anode side 21 of the oxygen generator 18. In contrast, nutrients are supplied from, and wastes and secreted insulin are removed from, the faces of the implantable device which are in contact with host cells/tissuelfluid (e.g., the faces of the cell encapsulation chamber 10 not in contact with the oxygen generator 18). The maximum total amount of cells 14 that can be viably maintained within the immunoisolation chamber 10 is the sum of that which can be substituted by each side of the device.

The oxygen generator 18 provides a continuous supply of reactant water from the surrounding host cells/tissue/fluids, continuous diffusion of generated gases out of the oxygen generator/electrolyzer 18, and exclusion of biological components that would otherwise contaminate the oxygen generator/electrolyzer 18. It is clear that the oxygen generator 18 can supply oxygen to the transplanted cells 14 at a $pO_2$ far higher than is possible from any physiological source. Furthermore, it is possible to completely prevent exposure of the transplanted system to the sustained hypoxic environment following transplantation. However, the $pO_2$ value should be optimized to limit oxygen toxicity that may result from chronic exposure at high $pO_2$.

In the instant invention, the rate of oxygen generated per unit area of the oxygen generator/electrolyzer 18 (oxygen flux, mol $O_2/cm^2 \cdot s$) is determined quantitatively by the current density between the anode layer 21 and cathode layer 23, which can be set at will to provide the optimum oxygen flux required to maintain the maximum viability of the cells 14. Factors such as the site of implantation and the local oxygen partial pressure ($pO_2$) in the blood, the spatial distribution of host blood vessels in the vicinity of the implant surface, the oxygen permeability of the semipermeable barrier layer 9, the oxygen consumption rate of the encapsulated cells 14, the geometrical characteristics of the implant system, and the tissue density and spatial arrangement of the encapsulated cells 14 will be considerations in optimizing oxygen flux.

The oxygen generation rate M (mol/s) of the electrolyzer is related to the applied current I (A) by $$I = n\, F\, M \quad (1)$$

where n=4 is the number of electrons required to make one molecule of oxygen, and F is Faraday's constant (96,500 A·s/equivalent). The imposed flux of oxygen $N_e$ from the oxygen generator/electrolyzer 18 into the cell encapsulating chamber/planar diffusion chamber 10 (mol/$cm^2 \cdot s$) is $$N_e = \frac{M}{A_e} \quad (2)$$

where $A_e$=0.317 $cm^2$ is the cross-sectional area of the gap between the oxygen genreator/electrolyzer 18 and the cell encapsulating chamber/diffusion chamber 10. Equation (1) can thus be written as $$i = n\, F\, N_e \quad (3)$$

where $i = I/A_e$ is the effective current density at the electrodes 21 and 23.

As discussed below, an understanding of oxygen diffusion and consumption in the system provides a framework to use to calculate the necessary parameters of the oxygen generator 18 which may be optimized to maximize oxygen generation and delivery to cells 14 while minimizing the size of the oxygen generator 18.

We consider one dimensional oxygen diffusion, perpendicular to the membranes 9 in Cartesian coordinates. Oxygen consumption is assumed to follow Michaelis-Menten kinetics with the local rate per unit volume V given by V=Vmax·(1−ε)·P/(Km+P) for P>$P_c$, where P is the local oxygen partial pressure, Vmax is the maximum oxygen consumption rate per unit volume of tissue, 1−ε is the live tissue volume fraction in the tissue layer, Km is the Michaelis-Menten constant, and $P_c$ is the critical value of P below which loss of tissue viability occurs due to hypoxia, and oxygen consumption ceases. We present here the analytical solution to the oxygen diffusion-reaction equation using zero-order kinetics (Km set equal to 0, V=Vmax (1−ε)=constant) and then examine the small difference that results from the solution obtained with numerical methods using the nonlinear Michaelis-Menten kinetics.

Assuming that all the tissue layer within the cell encapsulating chamber 10 is exposed to P>$P_c$, the solution for the local oxygen partial pressure is given by $$P(x) = \frac{P_{Se} + P_{Sm}}{2} + (P_{Se} - P_{Sm})\frac{x}{L} - \frac{V}{2D\alpha}\left[\left(\frac{L}{2}\right)^2 - x^2\right] \quad (4)$$

where x is the distance from the center plane of a tissue slab having a thickness L, considered positive in the direction towards the oxygen generator 18, $P_{Se}$ and $P_{Sm}$ are the values of P at the tissue-semiperrneable barrier layer 9 interfaces at the oxygen generator 18 and medium side, respectively, D is the effective diffusion coefficient of oxygen in tissue, and α is the Bunsen solubility of oxygen in tissue. $P_{Se}$ and $P_{Sm}$ are not known a priori but can be calculated in terms of the known quantities $N_e$ (the imposed oxygen flux from the oxygen generator/electrolyzer 18) and $P_{med}$ (the oxygen partial pressure in the medium bulk):

$$P_{Se} = P_{med} + (N_e - VL)R_{ext} \quad (5)$$

and $$P_{Se} = P_{med} + (N_e - VL)\left(\frac{L}{D\alpha} + R_{ext}\right) + \frac{VL^2}{2D\alpha} \quad (6)$$

where $R_{ext}$ is the sum of the diffusion resistances in series external to the tissue, i.e. those imposed by the semipermeable barrier layer 9 membrane laminate and boundary layer, given by $$R_{ext} = \frac{1}{k_c \alpha_{med}} + \left(\frac{L}{D\alpha}\right)_{M_2} + \left(\frac{L}{D\alpha}\right)_{M_1} \quad (7)$$

$M_1$ and $M_2$ refer to the cell 14 retentive and vascularizing membranes, respectively, $k_c = D_{med}/\delta_c$ is the boundary layer mass transfer coefficient between the stirred medium and the vascularizing membrane $M_2$, and $\delta_c$ is the concentration boundary layer thickness (including the outermost polyester mesh).

The maximum thickness of viable tissue $L_{max}$ that can be supported in the system is $$L_{max} = L_e + L_m \quad (8)$$

where $L_e$ and $L_m$ are the maximum tissue thicknesses that can be supported by the imposed oxygen flux and by oxygen diffusion from the bulk medium, respectively. $L_e$ can be calculated by making a mass balance around the tissue layer $$N_m = N_e - VL \quad (9)$$

and setting the oxygen flux at the tissue-semipermeable barrier layer 9 membrane interface at the medium side $N_m$ equal to 0:

$$L_e = \frac{N_e}{V} \quad (10)$$

$L_m$, equal to the distance from the tissue-semipermeable barrier layer 9 membrane interface at the medium side ($x_c=-L/2$) to the point where the oxygen flux is equals 0 and P=$P_c$, is given by $$L_m = -D\alpha R_{ext} + \left[(D\alpha R_{ext})^2 + \frac{2D\alpha}{V}(P_{med} - P_c)\right]^{1/2} \quad (11)$$

When the tissue thickness is not large enough for P to fall to $P_c$, the minimum value of oxygen partial pressure $P_{min}$ can be calculated in a similar way, by replacing $P_c$ by $P_{min}$ and $L_m$ by L−$L_e$ to yield $$P_{min} = P_{med} - V(L - L_e)R_{ext} - \frac{V}{2D\alpha}(L - L_e)^2 \quad (12)$$

This minimum occurs at distance $x_{min}$=L/2−$L_e$ from the tissue-semipermeable barrier layer 9 membrane interface at the oxygen generator/electrolyzer 18 side, provided that $L_e \leq L$.

For purpose of illustration, the oxygen partial pressure profiles were calculated in immunoisolated tissue supported on one face by an imposed oxygen flux from an oxygen generator 18 for the case that L≧$L_e$ so that P decreases to $P_c$ in the interior of the cell encapsulating chamber 10. Transport from the medium was not included. For zero-order kinetics, Equations (4) and (10) were used to calculate the maximum supportable thickness $L_e$, the local partial pressure P(z) where z=L/2−x, and the surface partial pressure $P_{Se}$. Calculation of the same dependent variables using Michaelis-Menten kinetics was carried out numerically. Parameter values selected for these calculations were 1−ε= 0.75, Vmax=2.76×$10^{-8}$ mol/$cm^3$·s, V=2.07×$10^{-8}$ mol/$cm^3$·s, Dα=1.70×$10^{-14}$ mol/$cm^3$·mm Hg·s, $^{22}$Pc=0.1 mm Hg, and Km=0.44 mm Hg. Oxygen partial pressures are plotted as a function of distance from the interface in FIG. 11 for values of imposed oxygen flux $N_e$ ranging from 1 to $10^{-10}$ mol/$cm^2$·s. These values of $N_e$ correspond to current densities i calculated from Equation (3) of 39 to 232 μA/$cm^2$ and to applied currents I of 12 to 73 μA(with $A_e$=0.317 $cm^2$ in our system). With increasing oxygen flux, both the interface partial pressure and the maximum thickness increase. The underprediction of P(z) by zero order as compared to Michaelis-Menten kinetics is hardly noticeable on the linear plot but is apparent on the semi-logarithmic plot (lower panel). At low partial pressures, the relative, but not the absolute, difference in P(z) can be large.

Figure 4:
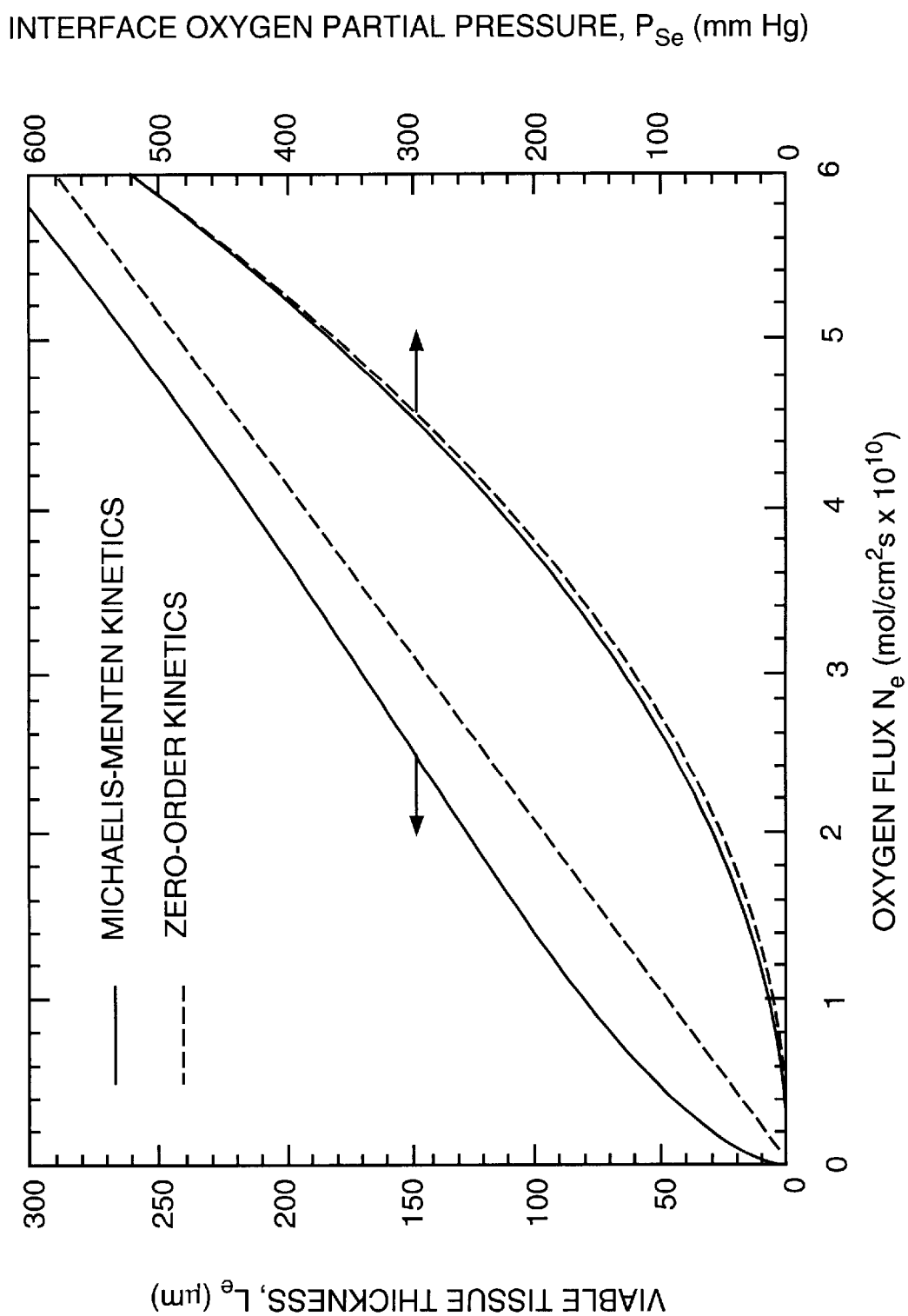
FIG. 4 shows a graph of viable tissue thickness vs. oxygen flux when using an oxygen generator according to one embodiment of the invention.

FIG. 4 is a plot of the interface oxygen partial pressure $P_{se}$ and the maximum viable tissue thickness supported by the oxygen generator/electrolyzer 18 $L_e$ as a function of the imposed oxygen flux $N_e$. At the highest oxygen flux investigated, $L_e$ is about 300 μm, and $P_{se}$ is about 500 mm Hg. Oxygen toxicity at these $P_{se}$ levels may be of concern with some cells and tissues, thereby setting a maximum limit on the imposed oxygen flux.

Figure 11:
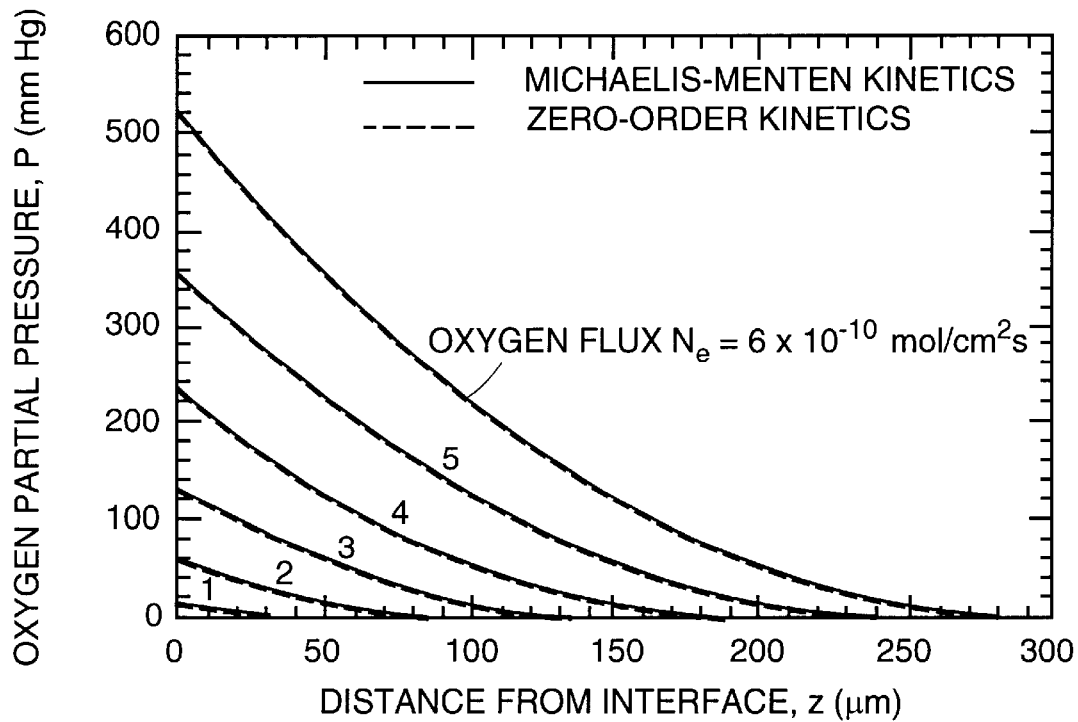
FIG. 11 shows a graph of oxygen partial pressure vs. distance from the oxygen generator/electrolyzer side/semipermeable barrier layer interface for different values of oxygen flux generated by the electrolyzer.
Figure 11:
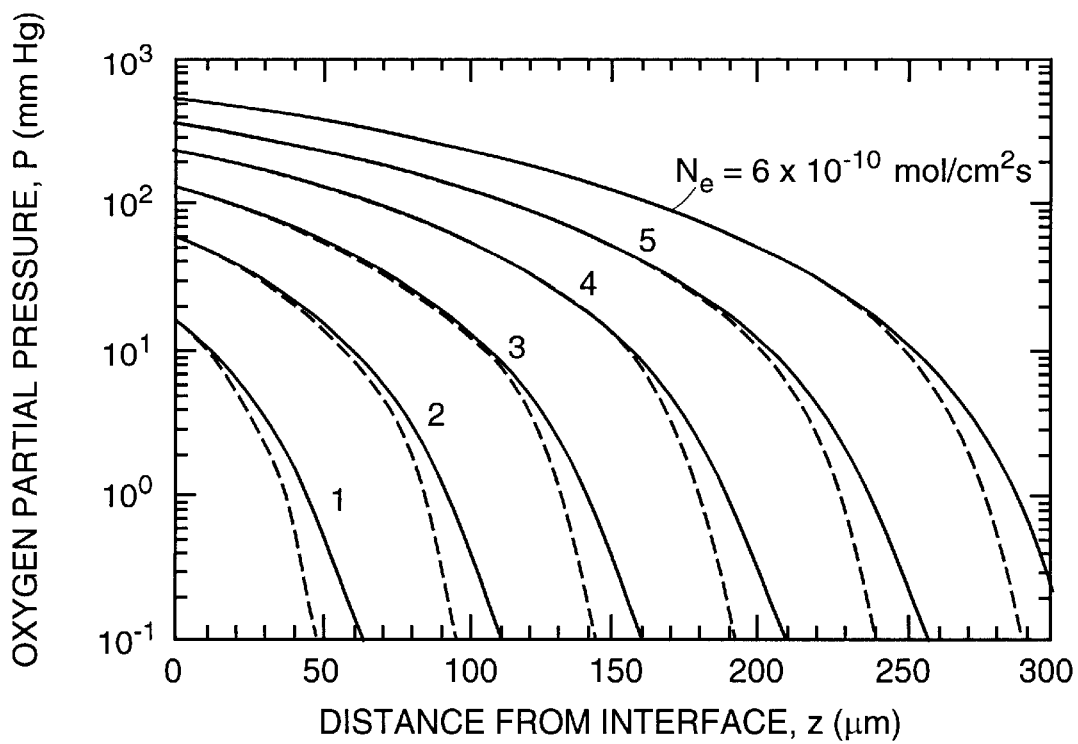

There is virtually no difference in FIG. 4 between the two predictions for $P_{se}$, but the zero-order model underpredicts $L_e$ by nearly 20 µm, except at very low $N_e$, as a consequence of the difference in profiles that develops at very low P(z) (FIG. 11). Because the error in estimating oxygen partial pressure profiles is negligible and the error in $L_e$ relatively small, the zero-order kinetic model is appropriate for optimizing performance of the oxygen generator 18.

The above parameters provide a means to calculate the optimal amount of oxygen generation that may be produced by a given oxygen generator 18.

While the production of oxygen by the oxygen generator 18 should be monitored and optimized, hydrogen production in vivo is not a problem. Hydrogen produced at the cathode side 23 of the oxygen generator 18 diffuses through the silicone rubber membrane 20 into the surrounding tissue to the bloodstream from which it is expelled in the lungs. Hydrogen is biologically inert in mammals under normal atmosphere conditions and is not oxidized by mammalian tissues under hyperbaric conditions.

In operation, the oxygen generator 18 is coupled to an energy source 199, such as a battery or a current controller. A small implanted battery with modest current densities and power requirements which is periodically recharged transcutaneously can provide a viable transplanted tissue thickness in excess of 200 µm based on mathematical models which describe oxygen diffusion and consumption in implanted immunobarrier devices. Given a $pO_2$ at the host-device interface or an imposed oxygen flux, the maximum tissue thickness (L) that can be supported by one face and the maximum $pO_2$ to which the tissue is exposed can be readily estimated. Using host interface values of 10, 40, and 100 mm Hg, and oxygen generation with maximum $pO_2$ of 100 and 300 mm Hg, the estimate for L is 22, 47, 78, 102, and 169 µm, respectively. Thus, the optimal total thickness supported is 78+169=247 µm, which would lead to a planar immunobarrier device having 1 cm$^3$ high-density tissue volume with a surface area of about 40 cm$^2$. The (maximum) oxygen flux would be about $5 \times 10^{-10}$ mole/cm$^2$·s, requiring a current density of 200 µA/cm2, very modest level, a total current of 8 mA, and about 16 mwatts (with power supplied at 2V DC).

In one embodiment of the invention, a source 199 of energy for the oxygen generator 18 is 2 AA-sized nickel-cadmium batteries. In this embodiment, the stored energy of about 450 mAh would require recharging after about 4 days. Button cells with up to 3600 mAh capacity are also encompassed within the scope of the invention and would require recharging every 4 weeks or so.

In a further embodiment of the invention, the recharging of an energy source 199 in communication with the oxygen generator 18 is performed transcutaneously. In one embodiment of the invention, this is achieved with a transcutaneous energy transfer (TET) system of the type developed to power implantable devices such as artificial hearts, left ventricular assist devices, defibrillators, and electrical stimulators which are well known in the art. These devices have been under development since the 1960s.

Figure 5:
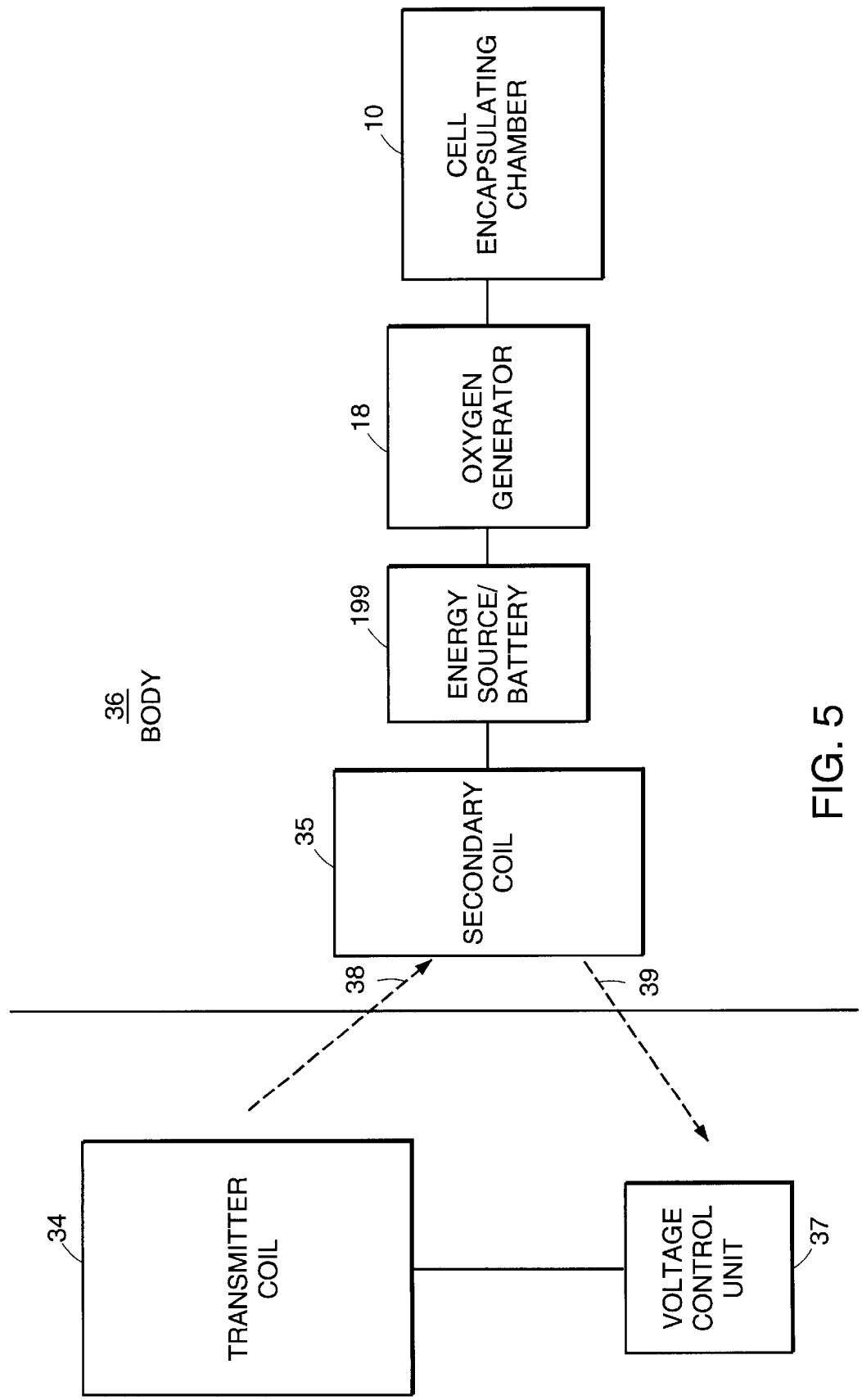
FIGS. 5 is a schematic TET system used with an oxygen generating device according to one embodiment of the invention.

Power from 5 to 70 watts has been transmitted through skin thicknesses of 3–15 mm at 60 to 80% efficiency using TET systems and implantable devices using TET systems can tolerate radial misalignments of up to 20 mm. In one embodiment of the invention, shown in FIG. 5, a TET system is provided which comprises a primary transmitter coil 34 and a secondary receiver coil 35. The primary coil 34 is outside of the body 36 and transmits a transmitted signal 38 to a secondary coil 35 inside the body 36. The secondary coil 35 is in communication with the energy source/battery 199, which in turn, is in communication with the oxygen generator 18 and can recharge energy within the energy source/battery 199. The TET system, thus ensures a continuous supply of energy to the oxygen generator 18, and therefore a continuous supply of oxygen, to the cell encapsulating chamber 10. In a further embodiment of the invention, a voltage control unit 37 is provided which controls the voltage and current in the primary coil 34 in response to a feedback signal 39 from the secondary coil 35. The TET secondary coil 35 can provide output voltages from 10 to 25 V for current loads of 0.5 to 4.0 amps. These capabilities greatly exceed the requirements for a biohybrid artificial pancreas. Thus, in one embodiment of the invention, a TET system is used for recharging implanted batteries on an overnight basis every few days (depending on implanted battery capacity). The TET system may also be worn continuously, using only small interchangeable external battery packs to drive the TET.

In another embodiment of the invention, the oxygen generator 18 may be used to provide supplemental oxygen to cells 14 in situ which are not encapsulated within a cell encapsulating device 10. In this embodiment of the invention, the oxygen generator 18 is implanted in the body in proximity to a desired site containing cells 14 for which supplemental oxygen is desired. In one embodiment of the invention, the oxygen generator 18 is provided in proximity to cells 14 encapsulated in microcapsules which are free to migrate within an intraperitoneal space. Methods of microencapsulating cells are well known in the art. In another embodiment, the oxygen generator 18 is provided in proximity to a cell-supporting, biocompatible, polymeric scaffold within the body of an organism, such as those used to fabricate artificial tissues. In all of these embodiments, the oxygen generator 18 may also be provided coupled to an energy source 199 such as a battery, which may be rechargeable by a recharging system, such as a TET system.

In another embodiment, the system is used to deliver oxygen in situ to cells 14 located at a distance from the oxygen generator 18. A tube with low oxygen permeability is attached to the oxygen generator 18. Generated oxygen is transferred through the tube to a flexible oxygen distributor fabricated from oxygen permeable membranes. In one aspect of the invention, the oxygen distributor is placed in proximity to cells, tissues, or organs, for which supplemental oxygen is desired. In another aspect of the invention, the oxygen distributor is placed in proximity to a cell encapsulating chamber 10. The flexible oxygen distributor provides a means to deliver oxygen from an oxygen generator 18 located at a distance to cells, tissues, or organs located anywhere, and having any shape within the body of an organism.

EXAMPLE 1

In vitro experiments in which βTC3 cells 14 are cultured in a cell encapsulating chamber 10 mated to an oxygen generator/electrolyzer 18 in a stirred flask have been performed. In this embodiment of the invention, the cell encapsulating chamber 10 was in the form of a ring immunoisolation chamber (shown schematically in FIG. 6) having a semipermeable barrier layer 9 membrane consisting of three layers: (a) a hydrophilic polytetrafluoroethylene (PTFE) inner membrane with nominal pore size of 0.45 µm and thickness of 25–35 µm (Biopore Millipore Corp, Bedford, Mass.), which retained cells and would function in vivo as an immunobarrier layer; (b) a hydrophobic PTFE outer membrane with nominal pore size of 5 μm and thickness of approximately 15 μM (W. L. Gore and Associates, Elkton, Md.), which would function in vivo as the vascularizing layer; and (c) a highly open outer meshwork about 125 μm thick of polyester fibers (about 50 μm in diameter) to provide support. The space between the two pieces of membrane was defined by a silicone rubber washer 33 (inner diameter 6.6 mm, cross-sectional thickness 100 μm after the device is compressed during assembly).

Cells 14 were cultured in Dulbecco's Modification of Eagle's Medium (DMEM, Mediatech, Hemdon, Va.) with 400 mg/dl glucose, supplemented by 10% (v/v) fetal bovine serum (FBS, HyClone, Logan, Utah), 100 IU penicillin, and 100 μg/ml streptomycin (Mediatech). Prior to loading the chamber, cells 14 were detached from T-flasks using trypsin-EDTA solution (Mediatech) and washed three times by centrifugation, removal of the supernatant, and resuspension in culture medium. After the first wash, cells 14 were suspended in 20 ml culture medium, and four aliquots of 200 μl each were taken, and counted in a hemocytometer with Trypan Blue staining. The average of these four counts was used to calculate the total cell 14 numbers in the original cell 14 sectional suspension. Only batches with viability greater than 95% were used for loading. After the final wash, a thin Pasteur pipette (made by pulling a regular Pasteur pipette over flame) was used to remove as much supernatant as possible without removing cells 14, and the cells 14 were resuspended in either phosphate buffered saline (PBS) or 1.7% (w/w) alginate solution to achieve the desired cell concentration. The suspension was carefully mixed without forming any air bubbles. A semipermeable barrier layer 9 consisitng of a laminated membrane was placed inside the titanium housing ring 32 with the hydrophilic side up and the silicone rubber washer 33 was placed on top of the membrane. A volume of 3.5 μl of cell 14 suspension was drawn into a 20 μl pipette tip and discharged at once on the center of the membrane. The other piece of membrane, with the hydrophilic side down, followed by the titanium sealing ring, were then placed on top of the cell 14 suspension, and the whole cell encapsulating ring chamber 10 was pressed together with a hand press. When alginate was used, the assembled cell encapsulating ring chamber 10 was immersed in 10 mM $BaCl_2$ solution for 30 seconds to crosslink the alginate. After three washes by immersion and shaking for 10 s in $Ca^{2+}$ and $Mg^{2+}$-free PBS, the loaded ring chamber was ready to be cultured in vitro. Prior to loading, sterilization was achieved by autoclaving the titanium rings 32 and washers 33, placing the oxygen generator/electrolyzer 18 in boiling water for at least 15 min, and immersing the semipermeable barrier layer 9 laminated membrane in 95% ethanol, 80% ethanol, and three times in PBS for at least 5 min in each. Sterilization was maintained by assembling the device in a laminar flow hood.

The cell encapsulating chamber 10 was oriented so that oxygen generation occurred below the bottom face of the ring immunoisolation chamber 10. The flask was then placed in an incubator and the oxygen generator 18 was connected to a power source 70 outside the incubator. Control experiments were carried out simultaneously with the oxygen generator 18 not connected to a power source 70.

The current was initially set at 11 $\mu A/cm^2$ corresponding to a maximum calculated tissue $pO_2$ of 77 mm Hg, and the current density was doubled every two days to account for cell growth. Culture medium was changed every two days. After 4 and 9 days, both control cells 14 and cells 14 provided with in situ oxygen generation were removed, embedded in paraffin, cut into 5 μm sections, and stained with hematoxylin.

Figure 7:
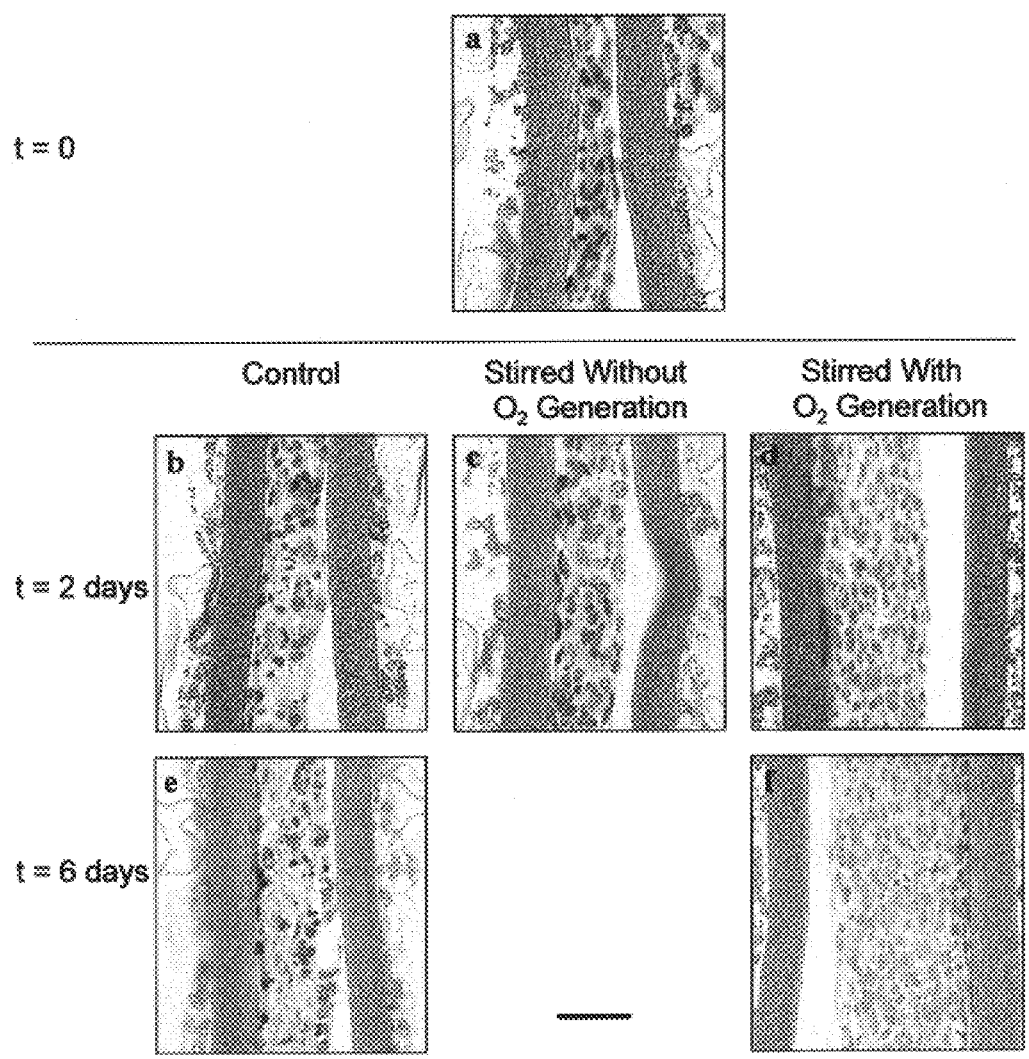
FIGS. 7a–f show photomicrographs of hemotoxylin-stained sections of βTC3 cells cultured in vitro in barium alginate within a planar immunoisolation chamber according to one embodiment of the invention.

Appropriate to this initial feasibility study, five runs were carried out comprising of 18 sets of in vitro experiments. In each run, the imposed oxygen flux (or a specified pattern of changes with time) and the number of cells intended to be added to the cell encapsulating chamber 10 (from a single cell 14 suspension) were held constant. Within a single run, each set of experiments included cell encapsulating chambers 10 cultured for a specific time period. A single set included experiments with, and without, oxygen generation with stirred medium. In some cases, controls were also carried out with neither oxygen generation nor stirring. Some sets of experiments were carried out with alginate in the cell encapsulating chambers 10, some without. Digital images taken from 5 μm paraffin sections through the device are presented here for three of the five runs. In runs 1 (FIG. 7) and 2 (FIG. 8), I=45 μA, $N_e$=3.7×10$^{-10}$ mol/cm²·s, and 2.3 or 2.5×10$^6$ cells 14 were intended to be added to the cell encapsulating chamber 10, respectively. In run 3 (FIG. 9), fewer cells 14 were intended to be added (0.35×10$^6$), and the low initial value of I=4.3 μA ($N_e$=0.35×10$^{-10}$ mol/cm²·s) was increased by a factor of √2 every 24 hr so as to parallel the doubling time of about 2 days observed with βTC3 cells 14 in culture.

In runs 1 and 3, three cell encapsulating chambers 10 were processed for histology immediately after being loaded in order to examine the initial cell 14 distribution. In all devices, cells 14 were usually distributed continuously within a region centered roughly around the center of the cell encapsulating chamber 10, with a diameter of about 2 to 3.5 mm. In run 1, the cell 14 layer ranged from one to four cells 14 (about 10 to 40 mm) thick and was usually thinnest at the periphery and thickest close to the center. FIG. 7a is a representative section of the layers observed.

Histological section from cell encapsulating chambers 10 that underwent culture for time t=1 to 9 days displayed cell 14 layer thickness patterns qualitatively similar to those at t=0. The sections selected for presentation here met the criteria of being in focus, having no sectioning artifacts, and being representative of the thickest cell 14 layer observed in the cell encapsulating chamber 10.

In run 1 (FIG. 7), initial (t=0) tissue thickness L was about 40 μm, and all cells 14 were alive. After 2 days culture, L≈45 μm in the control cell encapsulating chamber 10, with many condensed nuclei characteristic of apoptotic cells. In the stirred experiments without and with $O_2$ generation, L≈50 and 70 μm, respectively. Cell 14 viability was better with $O_2$ generation than without. After 6 days, L increased only to about 50 μm in the control cell encapsulating chamber 10, and there was substantial evidence of cell 14 death. With stirring and $O_2$ generation at 6 days, L increased to 100 μm and virtually all cells 14 were viable.

Figure 8:
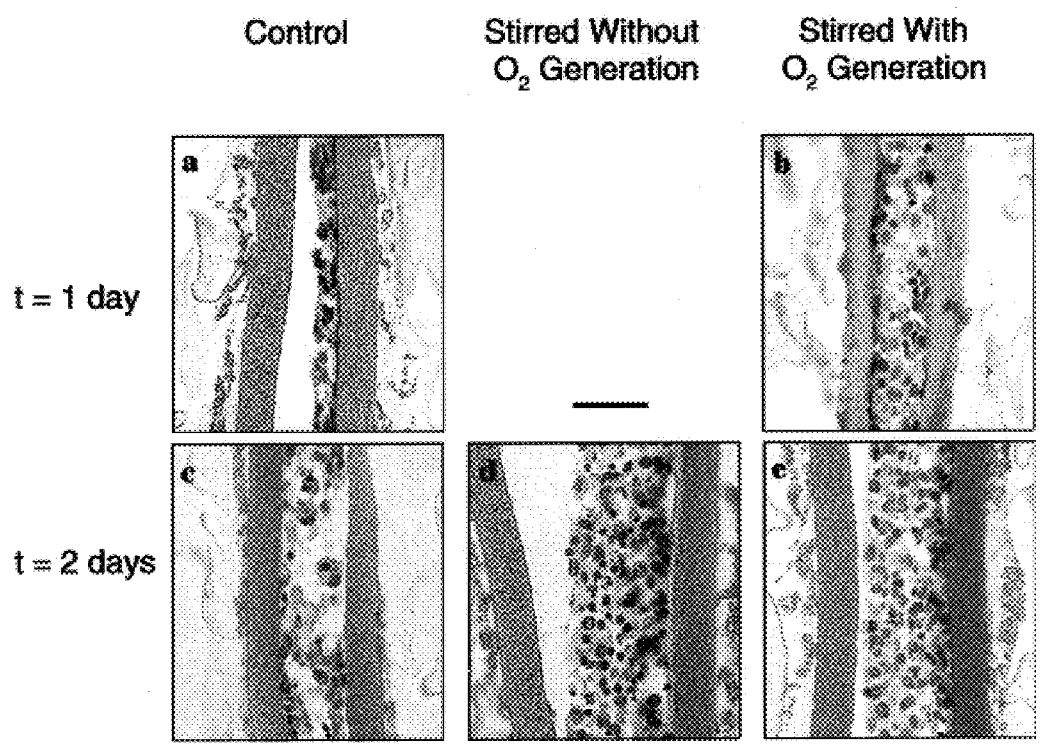
FIG. 8a–e show photomicrographs of hemotoxylin-stained sections of βTC3 cells cultured in vitro in barium alginate within a planar immunoisolation chamber according to another embodiment of the invention.

Results from run 2 are summarized in FIG. 8. After 1 day of culture, the control device had a tissue thickness of 20 μm, with substantial loss of cell 14 viability, whereas with stirring and $O_2$ generation L≈45 μm with much fewer dead cells 14. After 2 days in the control cell encapsulating chamber 10, L≈45 μm, but both the volume fraction and viability of cells 14 were very low. With stirring and without $O_2$ generation, L≈65 μm, but there were many apoptotic cells indicative of low cell viability. With $O_2$ generation, L≈60 μm, and virtually all cells were viable.

Figure 9:
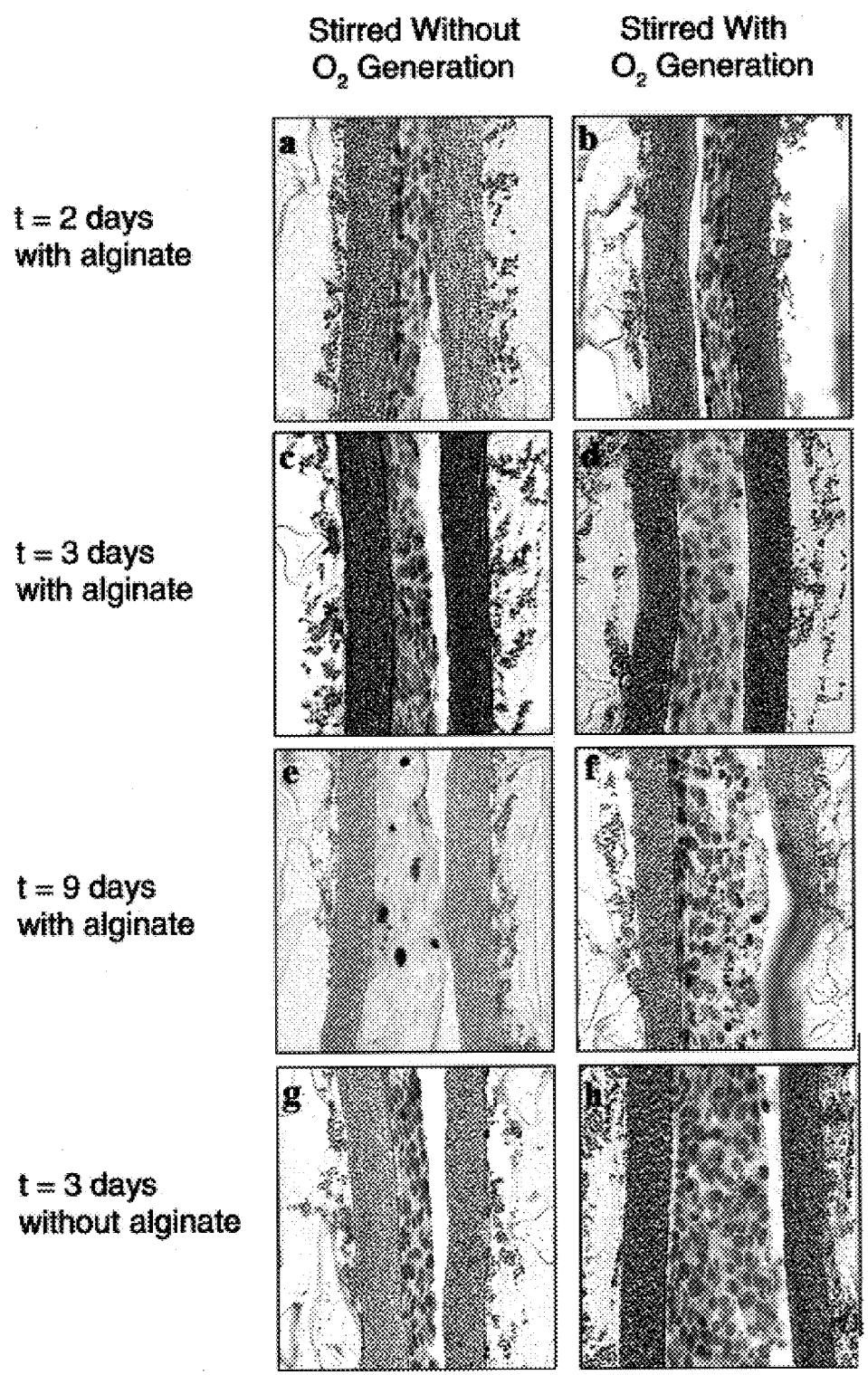
FIGS. 9a–h show photomicrographs of hemotoxylin-stained sections of βTC3 cells cultured in vitro in barium alginate within a planar immunoisolation chamber according to another embodiment of the invention.

FIG. 9 shows the results from stirred experiments in run 3, in which cell 14 loading and initial oxygen flux were much lower than in runs 1 and 2. At t=2 days, tissue thickness (L≈30 μm) and viability were similar with or without $O_2$ generation. At 3 days, L was still 25 μm without $O_2$ generation, while it increased to 50 μm with $O_2$ generation. At 9 days, most of cells 14 in the experiment without $O_2$ generation were dead. With $O_2$ generation, L≈70 μm, but there were apoptotic cells 14 and cell debris 14 near the semipermeable barrier layer 9 membrane adjacent to the oxygen generator/electrolyzer 18 where the oxygen partial pressure was highest. By 9 days and four doublings, $N_e$ had increased to the relatively high value of $5.6\times10^{-10}$ mol/$cm^2$·s, thereby suggesting the possibility of oxygen toxicity to the cells 14 nearest the oxygen generator/electrolyzer 18 in this experiment. Up to this point, all of the experiments presented were carried out with alginate. FIGS. 9g and 9h show results from experiments without alginate. Without $O_2$ generation, thickness was similar to that with alginate (L≈25 μm) after 3 days (FIG. 9c). With $O_2$ generation, L≈75 μm, higher than with alginate (FIG. 9d). It is possible that cross-linked alginate poses a restriction on cell growth.

In all of these experiments, the thickness of the cell 14 layer (and thus the growth rate of the cells 14), and their viability was highest in the stirred experiments with $O_2$ generation and lowest in the unstirred static controls (in which oxygen transport was most limited). These results verify the hypothesis that oxygen transport limitations can limit the growth and viability of cells 14 in immunobarrier devices. Furthermore, they demonstrate that in situ oxygen generation leading to an imposed oxygen flux into the tissue compartment can have a beneficial effect on cell 14 growth and viability.

The theoretical model developed earlier was used to analyze oxygen transport in nine of the experiments. Estimated values of parameters used in the calculations are summarized in Table 1. Each experiment is designated by its figure number. Vmax was based upon the value of 1.5 μmol/min·$10^9$ cells 14 for a monolayer of βTC3 cells 14 and converted to a volume basis for cells with $d_c$=12 μm to yield $2.76\times10^{-8}$ mol/$cm^3$·s. Permeability of the cells 14 was assumed to be the same as for islet tissue, $1.24\times10^{-14}$ mol/cm·mm Hg·s. The values of V and Dα varied between experiments because of variation in the tissue volume fraction 1-ε. Table 1 also contains estimates of the dependent variables $L_e$, $L_m$, $P_{Se}$, $P_{Sm}$, and $P_{min}$ which were calculated from Equations (10), (11), (6), (5), and (12), respectively.

The experiments analyzed represent three groups: (1) those with high imposed oxygen flux (experiments 7a, 7d, and 7f), (2) those with low oxygen flux (9b and 9h), and (3) those without oxygen flux (7a, 7c, 9a, and 9g). In the first group, $L_e$>L, and there is an efflux of unconsumed oxygen from the device, described by Equation (9). In the second group, $L_e$<L, and there is an influx of oxygen into the cell encapsulating chamber 10 from both sides, hence, a minimum in the P profile develops. In the third group, oxygen is supplied only from the medium, so the maximum value of P occurs at y=0 and $P_{min}$ occurs at z=0.

Although the bench-top current controller 40 used in our in vitro experiments is large because it provides displays and controls, we have also constructed a miniaturized controller 40 (6.5×3.5×5.4 cm) that can be worn by a rat. Furthermore, microelectronic technology can be used to make a miniaturized implantable device with a size suitable for implantation. The current can be preset or controlled by telemetry. We have calculated that an oxygen generation rate sufficient to support a biohybrid artificial pancreas in a human could be powered by a an implantable battery 199 with 3000 mAh capacity which would require recharging every four weeks. Recharging could be achieved with a transcutaneous energy transfer (TET) system of the type developed to power implantable devices such as artificial hearts, defibrillators, and electrical stimulators. The power transmission requirements for biohybrid artificial pancreas is many orders of magnitude smaller than the capacity of currently available TET systems.

EXAMPLE 2

Figure 10A:
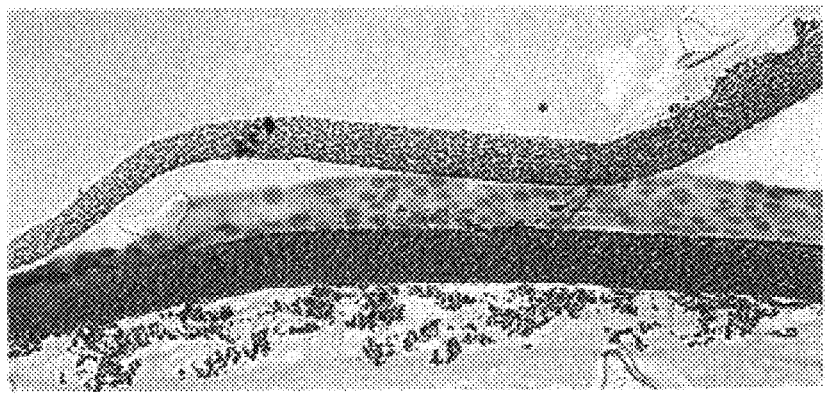
FIGS. 10a and 10b are photomicrographs of hemotoxylin-stained sections of an in vitro cultured planar immunoisolation chamber according to one embodiment of the invention loaded with rat islets (500 islets/device) in barium alginate.
Figure 10B:
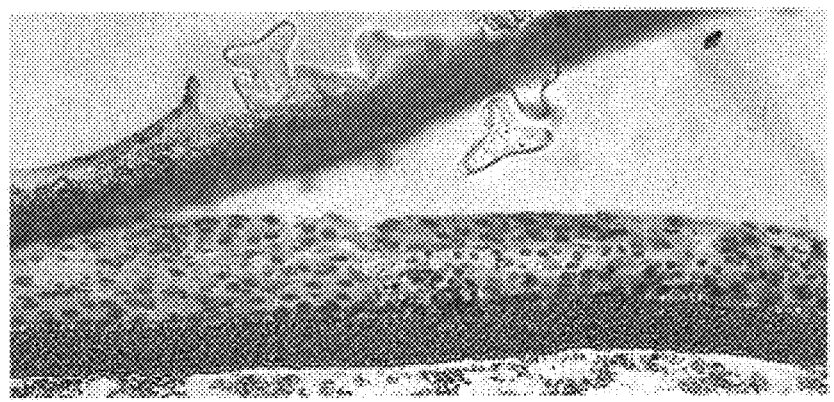

Islets isolated from Sprague-Dawley rats were used in another set of experiments. The loading density was 500 islets/cell encapsulating chamber 10. The current density, 100 μA/$cm^2$, which corresponds to a maximum predicted $pO_2$ of 300 mm Hg, was fixed at its initial value because islets do not proliferate. The result is shown in FIGS. 10a and 10b. After 4 days of culturing, the tissue thickness in the control experiment was only half of the tissue thickness in the experiment using in situ oxygen generation.

Although the examples above have been described in terms of transplantation of islets of Langerhans, it is generally applicable to implantation of any type of cells 14 or tissues for therapeutic application. The invention concerns a novel approach to improve growth and maintenance of cells 14 and to oxygenating cell 14-compatible fluids.

Having thus described certain embodiments of the present invention, various alterations, modifications, and improvements will be obvious to those skilled in the art. Such variations, modifications and improvements are intended to be within the spirit and scope of the invention. The materials employed, as well as their shapes and dimensions, generally can vary. Accordingly, the foregoing description is by way of example only and is not intended to be limiting.

TABLE 1

Values of important parameters in analyzed experiments

| Parameters | Experiments | | | | | | | | |
|---|---|---|---|---|---|---|---|---|---|
| Figure Number | 7a | 7a | 7c | 7d | 7f | 9a | 9b | 9g | 9h |
| Culture Time, t(d) | 0 | 0 | 2 | 2 | 6 | 2 | 2 | 3 | 3 |
| Oxygen Flux, N (mol/$cm^2$·s × $10^{10}$) | $0^a$ | $3.7^a$ | 0 | 3.7 | 3.7 | 0 | 0.50 | 0 | 0.70 |
| Tissue Thickness, L (μm) | 40 | 40 | 50 | 70 | 100 | 30 | 25 | 25 | 75 |
| Tissue Volume Fraction, 1-ε | 0.52 | 0.52 | 0.53 | 0.69 | 0.60 | 0.74 | 0.78 | 0.76 | 0.70 |
| Oxygen Consumption Rate, V (mol/$cm^3$·s × $10^8$) | 1.4 | 1.4 | 1.5 | 1.9 | 1.7 | 2.0 | 2.1 | 2.1 | 1.9 |
| Oxygen Permeability, Dα (mol/cm·mmHg·s × $10^{14}$) | 2.2 | 2.2 | 2.1 | 1.8 | 2.0 | 1.7 | 1.6 | 1.7 | 1.8 |
| Tissue Thickness Supportable | 0 | 250 | 0 | 190 | 220 | 0 | 23 | 0 | 37 |

TABLE 1-continued

Values of important parameters in analyzed experiments

| Parameters | Experiments | | | | | | | | |
|---|---|---|---|---|---|---|---|---|---|
| from Electrolyzer, $L_e$ (μm) | | | | | | | | | |
| Tissue Thickness Supportable from Medium, $L_m$ (μm) | 140 | 140 | 140 | 110 | 130 | 110 | 100 | 100 | 110 |
| Interface P at x = L/2, $P_{Se}$ (mmHg) | 116 | 313 | 108 | 340 | 356 | 115 | 144 | 120 | 115 |
| Interface P at x = −L/2, $P_{sm}$ (mmHg) | 122 | 250 | 116 | 224 | 212 | 121 | 141[b] | 124 | 116 |
| Minimum P, $P_{min}$ (mmHg) | — | — | — | — | — | — | 141[b] | — | 108 |

For all examples, $P_m = 142$ mm Hg, $R_{ext} = 3.5 \times 10^{11}$ mm Hg/(mol/cm$^2$.s), $\delta = 50$, $L_{M2} = 15$, and $L_{M1} = 30$ μm, $(D\alpha)_{med} = 3.5$, $(D\alpha)_{M2} = 2.8$, and $(D\alpha)_{M1} = 2.0 \times 10^{-14}$ mol/cm.mmHg.s, $D_{med} = 2.8 \times 10^{-5}$ cm$^2$/s, $\alpha_{med} = 1.3 \times 10^{-9}$ mol/cm$^3$.mmHg, Vmax $= 2.76 \times 10^{-8}$ mol/cm$^3$.s, $P_c = 0.1$ mm Hg, and Km $= 0.44$ mm Hg.
Calculations were carried out with three or more digits, but all parameter results, except for partial pressures, were rounded to two.
[a]The results at t = 0 correspond to the hypothetical oxygen profiles in the absence and presence of an imposed oxygen flux, respectively.
[b]$P_{Sm} - P_{min} \ll 0.5$ mm Hg

What is claimed is:

1. A method of delivering oxygen to a cell containment space, comprising:
   selecting a cell container defining a cell containment space for containing cells in vitro, wherein the cell container comprises a semipermeable barrier layer bounding at least a portion of the cell containment space;
   selecting an oxygen generator in communication with the containment space in proximity to the semipermeable barrier layer for generating oxygen from a fluid and delivering oxygen to the cell container, wherein the oxygen generator comprises an anode and a cathode, the anode and the cathode sandwiching a proton exchange membrane, the anode electrolyzes water to oxygen and hydrogen ions; and the cathode receives the hydrogen ions generated by the anode,
   wherein the proton exchange membrane transports the hydrogen ions from the anode to the cathode and oxygen is generated substantially without the generation of free hydrogen;
   initiating a chemical reaction comprising the electrochemical conversion of water in said fluid to oxygen; and
   permitting said oxygen to diffuse to said cell containment space.

2. The method of claim 1, wherein said oxygen is generated in situ in the body of an organism and delivered in the body.

3. The method of claim 1, wherein the oxygen generator is positioned in proximity to cells in said cell container.

4. The method of claim 3, wherein said cells are encapsulated.

5. The method of claim 1, further comprising at least one bioactive molecule in said cell container.

6. The method of claim 1, wherein the oxygen generator is in communication with an energy source.

7. The method of claim 1, further comprising the step of recharging the energy source.

8. The method according to claim 1 wherein said cell containment space of said cell container comprises a cell culture plate.

9. The method according to claim 1 wherein said cell containment space of said cell container comprises a tissue culture flask or cell culture flask.

10. The method according to claim 1 wherein said cell containment space of said cell container comprises a multi-well plate.

11. The method according to claim 1 wherein said oxygen generator is provided within or as an integral part of said cell container in an extracorporeal circuit device.

12. The method according to claim 1 wherein said oxygen generator is located at a distance from said cells in said cell containment space and oxygen is transferred from said oxygen generator through a tube attached to said oxygen generator to said cells in said cell containment space.

13. The method according to claim 1 wherein said oxygen is generated outside the body of an organism and delivered to cells within the body of an organism.

14. The method according to claim 1 wherein said oxygen is generated in vitro for delivery of oxygen to cells contained in an extracorporeal circuit.

15. The method according to claim 1 wherein said oxygen is generated in vitro for delivery of oxygen to cells within the body of an organism.

* * * * *

UNITED STATES PATENT AND TRADEMARK OFFICE
CERTIFICATE OF CORRECTION

| | | |
|---|---|---|
| PATENT NO. | : 6,368,592 B1 | Page 1 of 1 |
| APPLICATION NO. | : 09/356079 | |
| DATED | : April 9, 2002 | |
| INVENTOR(S) | : Colton et al. | |

It is certified that error appears in the above-identified patent and that said Letters Patent is hereby corrected as shown below:

Please insert the following in the specification of U.S. Patent No. 6,368,592 at column 1, line 3:

-- Sponsorship Information
This invention was made with government support under Grant Number R01 HD031443 awarded by the National Institutes of Health. The government has certain rights in the invention. --

Signed and Sealed this
Twenty-eighth Day of February, 2012

David J. Kappos
*Director of the United States Patent and Trademark Office*